(12) United States Patent
Weir et al.

(10) Patent No.: US 11,832,900 B2
(45) Date of Patent: *Dec. 5, 2023

(54) SYSTEMS AND METHODS FOR OPERATING AN END EFFECTOR

(71) Applicant: INTUITIVE SURGICAL OPERATIONS, INC., Sunnyvale, CA (US)

(72) Inventors: David W. Weir, San Carlos, CA (US); Grant Duque, San Jose, CA (US); Kevin Durant, Alameda, CA (US); Patrick Flanagan, San Diego, CA (US); Margaret M. Nixon, San Jose, CA (US); David W. Robinson, Los Altos, CA (US); John W. Zabinski, Fremont, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 179 days.

This patent is subject to a terminal disclaimer.

(21) Appl. No.: 17/306,721

(22) Filed: May 3, 2021

(65) Prior Publication Data

US 2021/0251702 A1 Aug. 19, 2021

Related U.S. Application Data

(63) Continuation of application No. 16/009,014, filed on Jun. 14, 2018, now Pat. No. 11,026,755, which is a (Continued)

(51) Int. Cl.
*A61B 34/00* (2016.01)
*A61B 90/00* (2016.01)
(Continued)

(52) U.S. Cl.
CPC .............. *A61B 34/25* (2016.02); *A61B 17/00* (2013.01); *A61B 17/07207* (2013.01);
(Continued)

(58) Field of Classification Search
CPC ... A61B 90/08; A61B 34/25; A61B 17/07207; A61B 34/37; A61B 90/06; A61B 17/28;
(Continued)

(56) References Cited

U.S. PATENT DOCUMENTS 966,177 A 8/1910 William
5,395,033 A 3/1995 Byrne et al.
(Continued)

FOREIGN PATENT DOCUMENTS

EP 0630612 A1 12/1994
EP 1728475 A2 12/2006
(Continued)

OTHER PUBLICATIONS

Hamel et al., Large Scale Multi-Fingered End-Effector Teleoperation, 2009, IEEE, p. 3304-3310 (Year: 2009).*
(Continued)

*Primary Examiner* — McDieunel Marc
(74) *Attorney, Agent, or Firm* — Artegis Law Group, LLP

(57) ABSTRACT

Systems and methods for operating an end effector include an end effector for grasping a material, a drive system coupled to the end effector, and a processor. The processor is configured to use the drive system to grasp a material using the end effector, determine a grasping separation parameter of the end effector, determine, based on the determined grasping separation parameter, a prediction of success or failure in configuring the end effector for firing a staple through the material, and based on the determined
(Continued)

grasping separation parameter, output an indicator of whether it is safe to proceed with stapling of the material grasped by the end effector.

20 Claims, 24 Drawing Sheets

Related U.S. Application Data continuation of application No. 15/364,114, filed on Nov. 29, 2016, now Pat. No. 9,999,472, which is a continuation of application No. 14/635,866, filed on Mar. 2, 2015, now Pat. No. 9,662,177, which is a continuation of application No. 13/350,502, filed on Jan. 13, 2012, now Pat. No. 8,989,903.

(60) Provisional application No. 61/443,159, filed on Feb. 15, 2011.

(51) Int. Cl.
| | |
|---|---|
| A61B 17/072 | (2006.01) |
| A61B 17/00 | (2006.01) |
| A61B 17/28 | (2006.01) |
| B25J 9/16 | (2006.01) |
| A61B 34/37 | (2016.01) |
| A61B 17/29 | (2006.01) |
| G06F 3/14 | (2006.01) |
| A61B 34/30 | (2016.01) |
| G06F 3/01 | (2006.01) |
| G06F 3/16 | (2006.01) |

(52) U.S. Cl.
CPC .............. *A61B 17/28* (2013.01); *A61B 17/29* (2013.01); *A61B 34/37* (2016.02); *A61B 90/06* (2016.02); *A61B 90/08* (2016.02); *B25J 9/1694* (2013.01); *G06F 3/14* (2013.01); *A61B 34/30* (2016.02); *A61B 2017/00115* (2013.01); *A61B 2017/00132* (2013.01); *A61B 2017/2808* (2013.01); *A61B 2034/254* (2016.02); *A61B 2034/301* (2016.02); *A61B 2090/064* (2016.02); *A61B 2090/0811* (2016.02); *G06F 3/016* (2013.01); *G06F 3/16* (2013.01)

(58) Field of Classification Search
CPC . A61B 17/29; A61B 7/00; A61B 2017/00132; A61B 2090/064; A61B 34/30; A61B 2090/0811; A61B 2017/2808; A61B 2017/00115; A61B 2034/254; A61B 2034/301; G06F 3/14; G06F 3/016; G06F 3/16; B25J 9/1694
See application file for complete search history.

(56) References Cited

U.S. PATENT DOCUMENTS

| | | | |
|---|---|---|---|
| 5,728,599 A | 3/1998 | Rostoker et al. | |
| 5,855,553 A | 1/1999 | Tajima et al. | |
| 5,916,146 A | 6/1999 | Allotta et al. | |
| 6,594,552 B1 | 7/2003 | Nowlin et al. | |
| 6,785,593 B2 | 8/2004 | Wang et al. | |
| 6,799,088 B2 | 9/2004 | Wang et al. | |
| 6,836,703 B2 | 12/2004 | Wang et al. | |
| 6,839,612 B2 | 1/2005 | Sanchez et al. | |
| 6,879,880 B2 | 4/2005 | Nowlin et al. | |
| 6,889,116 B2 | 5/2005 | Jinno | |
| 6,892,112 B2 | 5/2005 | Wang et al. | |
| 7,043,338 B2 | 5/2006 | Jinno | |
| 7,373,219 B2 | 5/2008 | Nowlin et al. | |
| 7,454,268 B2 | 11/2008 | Jinno | |
| 7,778,733 B2 | 8/2010 | Nowlin et al. | |
| 8,594,841 B2 | 11/2013 | Zhao et al. | |
| 8,640,788 B2 | 2/2014 | Dachs, II et al. | |
| 8,641,713 B2 | 2/2014 | Johnson et al. | |
| 8,852,174 B2 | 10/2014 | Burbank | |
| 8,876,857 B2 | 11/2014 | Burbank | |
| 8,893,946 B2 | 11/2014 | Boudreaux et al. | |
| 8,989,903 B2 | 3/2015 | Weir et al. | |
| 9,662,177 B2 | 5/2017 | Weir et al. | |
| 9,814,530 B2 | 11/2017 | Weir et al. | |
| 9,999,472 B2 * | 6/2018 | Weir ....................... | A61B 17/28 |
| 2003/0135204 A1 | 7/2003 | Lee et al. | |
| 2005/0192609 A1 | 9/2005 | Whitman et al. | |
| 2006/0273135 A1 | 12/2006 | Beetel | |
| 2007/0005045 A1 | 1/2007 | Mintz et al. | |
| 2007/0142823 A1 | 6/2007 | Prisco et al. | |
| 2008/0232932 A1 | 9/2008 | Jinno | |
| 2009/0188094 A1 | 7/2009 | Cunningham et al. | |
| 2009/0192523 A1 | 7/2009 | Larkin et al. | |
| 2010/0198220 A1 | 8/2010 | Boudreaux et al. | |
| 2010/0228250 A1 | 9/2010 | Brogna | |
| 2010/0332031 A1 | 12/2010 | Itkowitz et al. | |
| 2011/0118707 A1 | 5/2011 | Burbank | |
| 2011/0118708 A1 | 5/2011 | Burbank et al. | |
| 2014/0052154 A1 | 2/2014 | Griffiths et al. | |
| 2015/0238269 A1 * | 8/2015 | Weir ....................... | A61B 34/25 |
| | | | 700/264 |
| 2016/0074036 A1 * | 3/2016 | Weir .................. | A61B 17/0686 |
| | | | 606/151 |
| 2016/0128790 A1 | 5/2016 | Ogawa et al. | |
| 2016/0144504 A1 | 5/2016 | Kuth et al. | |
| 2016/0175060 A1 | 6/2016 | Park | |
| 2016/0199981 A1 | 7/2016 | Atohira et al. | |
| 2017/0071679 A1 * | 3/2017 | Weir ....................... | A61B 17/29 |
| 2018/0325606 A1 | 11/2018 | Weir et al. | |

FOREIGN PATENT DOCUMENTS

| | | |
|---|---|---|
| EP | 2127604 A1 | 12/2009 |
| JP | 2004514490 A | 5/2004 |
| WO | WO-0243571 A2 | 6/2002 |
| WO | WO-03020139 A2 | 3/2003 |
| WO | WO-2005112808 A1 | 12/2005 |
| WO | WO-2012112251 A1 | 8/2012 |

OTHER PUBLICATIONS

Doulgeri et al., Picking up flexible pieces out of a bundle, 2002, IEEE, p. 9-19 (Year: 2002).*
Bowers et al., Manipulation of unmodeled objects using intelligent grasping schemes, 2003, IEEE, p. 320-329 (Year: 2003).*
Karakerezis et al., A robotic gripping system with consideration of grasping flat non-rigid materials, 2002, IEEE, p. 936-941 (Year: 2002).*
Tsukune et al., Effect of the thickness and nonlinear elasticity of tissue on the success of surgical stapling for laparoscopic liver resection, 2014, IEEE, p. 353-356 (Year: 2014).*
Benjcxy., et al., "Sensor Fusion In Telerobotic Task Controls," 1995, IEEE, pp. 241-249.
Brown R., et al., "A 3d Modeular Gripper Design Tool," Proceedings of the 1997 IEEE International Conference on Robotics and Automation, Apr. 1997, pp. 2332-2339.
Cleary, Kevin et al., "State of the Art in Surgical Robotics:Clinical Applications and Technology Challenges," Computer Aided Surgery, 2001 [retrieved on Feb. 24, 2002], pp. 1-26.
Extended European Search Report for Application No. EP17205277.1, dated Feb. 23, 2018, 7 pages (ISRG02980D1/EP).
Extended European Search Report for Application No. EP21154113.1 dated Mar. 5, 2021, 8 pages.
Hamel., et al., "Large Scale Multi-fingered End-effect or Teleportation," 2009, IEEE, pp. 3304-3310.
Houshangi., et al., "Control of a Robotic Manipulator to Grasp a Moving Target Using Vision," 1990, IEEE, pp. 604-615.
Ikuta K., et al., "Hyper Redundant Miniature Manipulator Hper Finger for Remote Minimally Invasive Surgery in Deep Area,"

(56) References Cited

OTHER PUBLICATIONS

Proceedings of the 2003 IEEE International Conference on Robotics and Automation, Taipeo, Taiwan, Sep. 14-19, 2003, pp. 1098-1102.

Lii., et al., "Toward understanding the effects of visual- and force-feedback on robotic hand grasping performance for space Teleoperation," 2010, IEEE, pp. 3745-3752.

Mack, Michael J. et al., "Minimally Invasive and Robotic Surgery," JAMA, 2001, pp. 568-572, vol. 285—Issue 5.

Ottaviano E., et al., "Grasp Force Control in Two-Finger Grippers with Pneumatic Actuation," Proceedings of the 2000 IEEE International Conference on Robotics and Automation, Apr. 2000, pp. 1976-1981.

PCT/US12/021342 International Search Report and Written Opinion of the International Searching Authority, dated Mar. 30, 2012, 15 pages.

PCT/US2012/021319 International Search Report and Written Opinion of the International Searching Authority, dated Mar. 30, 2012, 13 pages.

Puangmali P., et al., "State-of-the-Art in Force and Tactile Sensing for Minimally Invasive Surgery," IEEE Sensors Journal, Apr. 2008, vol. 8 (4), pp. 371-381.

Tholey G., et al., "A Modular, Automated Laparoscopic Grasper with Three-Dimensional Force Measurement Capability, "IEEE International Conference on Robotics and Automation, Apr. 2007, pp. 250-255.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

SYSTEMS AND METHODS FOR OPERATING AN END EFFECTOR

CROSS-REFERENCES TO RELATED APPLICATIONS

The present application is a continuation of U.S. patent application Ser. No. 16/009,014, filed Jun. 14, 2018, which is a continuation of U.S. patent application Ser. No. 15/364,114, filed Nov. 29, 2016 and now U.S. Pat. No. 9,999,472, which is a continuation of U.S. patent application Ser. No. 14/635,866, filed Mar. 2, 2015 and now U.S. Pat. No. 9,662,177, which is a continuation of U.S. patent application Ser. No. 13/350,502, filed Jan. 13, 2012 and now U.S. Pat. No. 8,989,903, and claims priority to U.S. Provisional Patent Application No. 61/443,159, filed Feb. 15, 2011, the entire contents of each being incorporated herein by reference.

The present application is related to U.S. application Ser. No. 12/705,418 entitled "Cut and Seal Instrument," filed on Feb. 12, 2010; U.S. Provisional Application No. 61/260,907, entitled "END EFFECTOR WITH REDUNDANT CLOSING MECHANISMS," filed on Nov. 13, 2009; U.S. Provisional Application No. 61/260,903, entitled "WRIST ARTICULATION BY LINKED PENSION MEMBERS," filed on Nov. 13, 2009; U.S. Provisional Application No. 61/260,915, entitled "SURGICAL TOOL WITH A TWO DEGREE OF FREEDOM WRIST," filed on Nov. 13, 2009; and U.S. Provisional Application No. 61/260,919, entitled "MOTOR INTERFACE FOR PARALLEL DRIVE SHAFTS WITHIN AN INDEPENDENTLY ROTATING MEMBER," filed on Nov. 13, 2009; each of which is incorporated herein by reference in its entirety.

BACKGROUND OF THE INVENTION

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which includes minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure by means of a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems have been recently been developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing an image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

A huge variety of tools have been developed for open surgery, many (though not necessarily all) of which have been successfully modified for minimally invasive surgical procedures. For example, manual clamps, linear cutters, and stapling devices can apply significant therapeutic clamping forces on tissues, which can enhance a variety of surgical procedures. Unfortunately, work in connection with the present invention indicates that adapting open surgical clamping devices (and developing methods for safely and effectively using them) within minimally invasive settings may be more challenging than expected. In particular, developing and using surgical clamping jaws capable of generating desired clamping force while also providing the desired maneuverability for use within size-restricted minimally invasive surgical access and treatment sites has proven to be quite difficult. Transferring the advantages available from surgical staplers, linear cutters, and surgical clamping tools to robotic surgical settings may involve even more challenges, particularly given the different paradigms in surgeon-directed tool movement, tool activation, and physician feedback presented by the new telesurgical treatment systems.

Thus, there is believed to be a need for improved methods and systems for surgical staplers, linear cutters, and/or other clamping surgical tools. Such tools may be beneficial in a wide range of surgical applications, particularly in minimally invasive and/or robotic surgical applications.

BRIEF SUMMARY OF THE INVENTION

Improved systems and methods to facilitate clamping are provided. The claimed methods and system can be used to help predict whether clamping a body tissue grasped between jaws at a desired clamping force is likely to be successful before attempting to clamp. The claimed systems and methods are particularly useful in surgical applications involving clamping of a body tissue between two jaws of an end effector. Many surgical applications involve clamping of a body tissue at a clamping force sufficient for cutting, sealing and/or stapling of the clamped tissue. Since high force clamping may potentially damage tissues if clamping fails, the present methods and systems are particularly advantageous as they indicate a prediction as to the likelihood of clamping success before clamping is attempted.

While the various embodiments disclosed herein are primarily described with regard to surgical applications, these surgical applications are merely example applications, and the disclosed end effectors, tools, and methods can be used in other suitable applications, both inside and outside a human body, as well as in non-surgical applications.

In a first aspect, the invention provides a method of indicating whether clamping of a tissue grasped between a first and second jaw is likely to be successful. The method includes determining and/or measuring a separation between two jaws grasping a tissue at a grasping force and, in response to the determination of the separation, outputting on a user interface an indication of a prediction of whether clamping of the grasped tissue at a desired clamping force is likely to be successful. In such methods, the clamping force is greater than the grasping force and, in some embodiments, the clamping force may comprise a first predetermined range of forces, each larger than the grasping force. The indicator of whether clamping success is likely may also comprise an indicator whether clamping success at a desired clamping force and at a desired clamping separation is likely. The desired clamping separation may comprise a predetermined range of separations. Furthermore, the separation may be expressed in terms of a separation angle between the first and second jaw or a separation distance between jaw members. In many embodiments, the desired clamping separation is suitable for firing a staple of a given size through the tissue clamped between the jaws, cutting the grasped tissues, and/or sealing the grasped tissue. The first and second jaws will typically be part of an end effector. The first and second jaw may comprise a first jaw articulable against a portion of the end effector, in which case the portion of the end effector comprises the second jaw. In certain embodiments, the prediction may be based also on the stiffness of the tissue. The stiffness of the tissue may be input, if known, or may be estimated based on the grasping force and separation or on the rate of change of separation as the grasping force is applied. For example, the estimation of stiffness may be based on an empirically derived relationship between these factors and tissue stiffness.

The claimed methods provide an indication of clamping success and/or clamping failure in response to a separation parameter between a first and second jaw, the first and second jaw having a body tissue grasped therebetween. In some embodiments, the indication is provided in response to the separation parameter and the grasping force. One embodiment of the method includes grasping the tissue with the first and second jaw, typically in response to a command from a user. The method further includes clamping the tissue between the first and second jaw at the clamping force, after the system provides an indicator that clamping success is likely. The system clamps the tissue typically in response to a command from a user to clamp the tissue, after the system has provided an indication of whether clamping success or failure is likely. One embodiment of the claimed method includes releasing the grasped tissue after the system has provided an indication of a prediction of clamping failure. The system releases the grasped tissue typically in response to a command from a user to release the tissue from between the jaws.

In another aspect, the system and methods include a soft grip mode, in which the first and second jaw grasp a body tissue at a grasping force, and a clamping mode, wherein the first and second jaw clamp the grasped body tissue at a clamping force, the clamping force being greater than the grasping force. A mechanism coupled with the jaws causes the jaws to close so as to grasp and/or clamp the body tissue between the first and second jaw. The mechanism may be one mechanism coupled with an actuator, such as a motor, or, alternatively, the mechanism may comprise multiple mechanisms for exerting forces of differing magnitudes. The actuator may comprise an actuator system including one or more actuators. An actuator maybe any or all of an electric motor, a hydraulic actuator, a pneumatic actuator, and a variable torque output actuator. In embodiments having a soft grip mode and a clamping mode, the system typically switches between modes in response to a user command after the system has provided an indication that clamping of the grasped tissue would likely be successful.

In most embodiments, the separation parameter is measured and/or determined by the system during application of a grasping force or torque. The system may determine/measure the separation between jaw members from positional data obtained by the robotic system controlling the jaw members, such as a robotic patient-side manipulator (PSM) system, for example, described in U.S. patent application Publication No 2007/0005045, the entire contents of which are incorporated herein by reference. Typically, the clamping force is at least twice that of the grasping force, preferably about 5 to 10 times greater than the grasping force.

In another aspect of the invention, the indication of the clamping prediction is provided on a user interface. Preferably, the indication is a visual indicator superimposed over a display providing images of the surgical tools during a surgical procedure. In other embodiments, the indication of the clamping prediction may be any of an audio, visual or sensory indicator so as to communicate to the user a prediction of whether clamping is likely to be successful. In another aspect of the invention, the indication of clamping prediction may further include an indication of whether it is safe to initiate a stapling action. For example, after a prediction that clamping is likely and clamping has been completed, a timer may be initiated such that once a predetermined amount of time has elapsed after successful clamping, an indicator is displayed over the display that it is safe to proceed stapling into the clamped tissue. A clamping timing indicator may be advantageous as it may reduce the amount of clamped tissue over time or reduce the amount of fluid within the tissue so as to reduce bleeding during stapling and help achieve hemostasis. The timing indicator may also track elapsed time of clamping after stapling of the clamped tissue so as to reduce bleeding or to aid in achieving hemostasis of the stapled tissue.

In another aspect, the prediction of clamping is provided in response to the separation parameter between grasped jaws as determined and/or measured by the system. In many embodiments, if the measured separation is greater than a threshold or a desired grasping separation parameter, then the prediction is indicative of likely clamping failure, while if the grasping separation is equal to or less than the desired grasping separation parameter, the prediction is indicative of likely clamping success. In some embodiments, the threshold or desired grasping separation parameter may be based in part on an apparent or estimated tissue stiffness. The desired separation may comprise either an angle between jaws or a distance between jaws, and the separation parameter may be a discrete parameter or a predetermined range of values. For many applications, the threshold or desired grasping separation is an angle of about 8 degrees or a distance of about 6 mm between tips of the jaw members. In one embodiment, a 4 degree angle results in a gap of approximately 3 mm between the tips of the jaws. In general, when the tissue is successfully clamped, the gap between jaws is between 1.3 mm to 2 mm, although one of skill in the art would appreciate that this value may vary depending on the application. In embodiments where the desired separation parameter is a predetermined range, clamping success may be indicated when the measured separation is within the predetermined range. For example, a predetermined range of desired grasping separation parameters may be from 1 to 10 degrees, preferably 1 to 8 degrees, or, in terms of distance, the range of desired grasping separation parameters from 0.7 mm to 8 mm, preferably 2 to 5 mm. Ideally, the desired target separation is approximately 4 mm. The desired separation values or ranges may vary according to any number of variables, including but not limited to: a dimension of the first or second jaw, a staple length, a staple size, a stapler angle of articulation, a thickness of the body tissue, a type of body tissue, a characteristic of the body tissue the desired clamping force or the desired clamping separation. In many embodiments, the grasping force between the tips of the jaws will be within a range from about 3 lb-f to 10 lb-f, preferably about 5 lb-f, and the clamping force between the tips of the jaws will be within a range from about 30 to 70 lb-f, preferably about 50 lb-f. The grasping force and desired clamping force may vary according to any of the above variables or by the type of surgical application (e.g. tissue cutting, sealing of tissue, and/or stapling of tissue).

In another aspect, the present invention includes a system for performing the claimed methods. Ideally, the system comprises a first and second jaw, a drive system coupled to the jaws, a user interface, and an electronic data processor coupled to the drive system. In many embodiments, the drive system closes the jaws on tissue at a predetermined grasping force, the electronic data processor measures a distance between the jaws, and based on the measured distance between the jaws, the electronic data processor outputs to the user interface a prediction of success of clamping the tissue between the two jaws at a desired clamping force, wherein the clamping force is within a first predetermined range that is larger than the grasping force, and wherein the clamped jaw separation distance is within a second predetermined range. Ideally, the second predetermined range comprises a distance between the jaws that is suitable for applying a staple to the tissue between the jaws.

The system may also comprise one or more modes of operation. In some embodiments, the system comprises a soft grip mode and a clamping mode. In the soft grip mode, the jaws close or close so as to grasp the body tissue at the predetermined grasping force. In the clamping mode, the jaws close so as to clamp the body tissue at the clamping force. Typically, the system only provides a prediction of clamping success when in the grasping mode, such that a surgeon may grasp tissue in the grasping mode in preparation for clamping the grasped tissue. In embodiments having multiple modes, the system may further include a controller for switching between modes.

The system may include an actuator system coupled with the jaws through a mechanism for effecting movement of the jaws so as to grasp and/or clamp the body tissue. In some embodiments, the mechanism may include cables and a linkage. In many embodiments, the mechanism comprises a lead screw and cam. In some embodiments, particularly in embodiments having multiple modes, a first mechanism effects grasping of the jaw and a second mechanism effects clamping with the jaws. For example, the first mechanism may comprise cables and the second mechanism may comprise a lead screw. Effecting grasping with cables would be ideal for providing a fast response with a relatively low force, while a lead screw would be more suited for provided a higher force despite having a longer response time. The first actuation mechanism can provide a low force for grasping the body tissue between jaw members, and the second actuation mechanism can provide a high clamping force mode. For example, in many embodiments, the maximum clamping force of the movable jaw provided by the second actuation mechanism is larger than a maximum grasping force provided by the first actuation mechanism.

The first and second actuation mechanisms can employ different force transmission mechanisms corresponding with the force requirements for the low force grasping mode and the high force clamping mode. For example, a force used by the first jaw actuation mechanism to move the jaw from the open to the close position can include a linear force, and a force used by the second jaw actuation mechanism to move the jaw from the open to the closed position can include a torque. In many embodiments, the first jaw actuation mechanism for use in the low force grasping mode includes a cable-driven mechanism, with the second jaw actuation mechanism for use in the high force clamping mode includes a leadscrew-driven mechanism.

Any of the above described methods may be used in the clamping of any material and may be used in application that are non-surgical in nature. For example, the above described methods may be used to indicate to a user a clamping prediction regarding the clamping of a flexible compliant material in an industrial process.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

Figure 1:
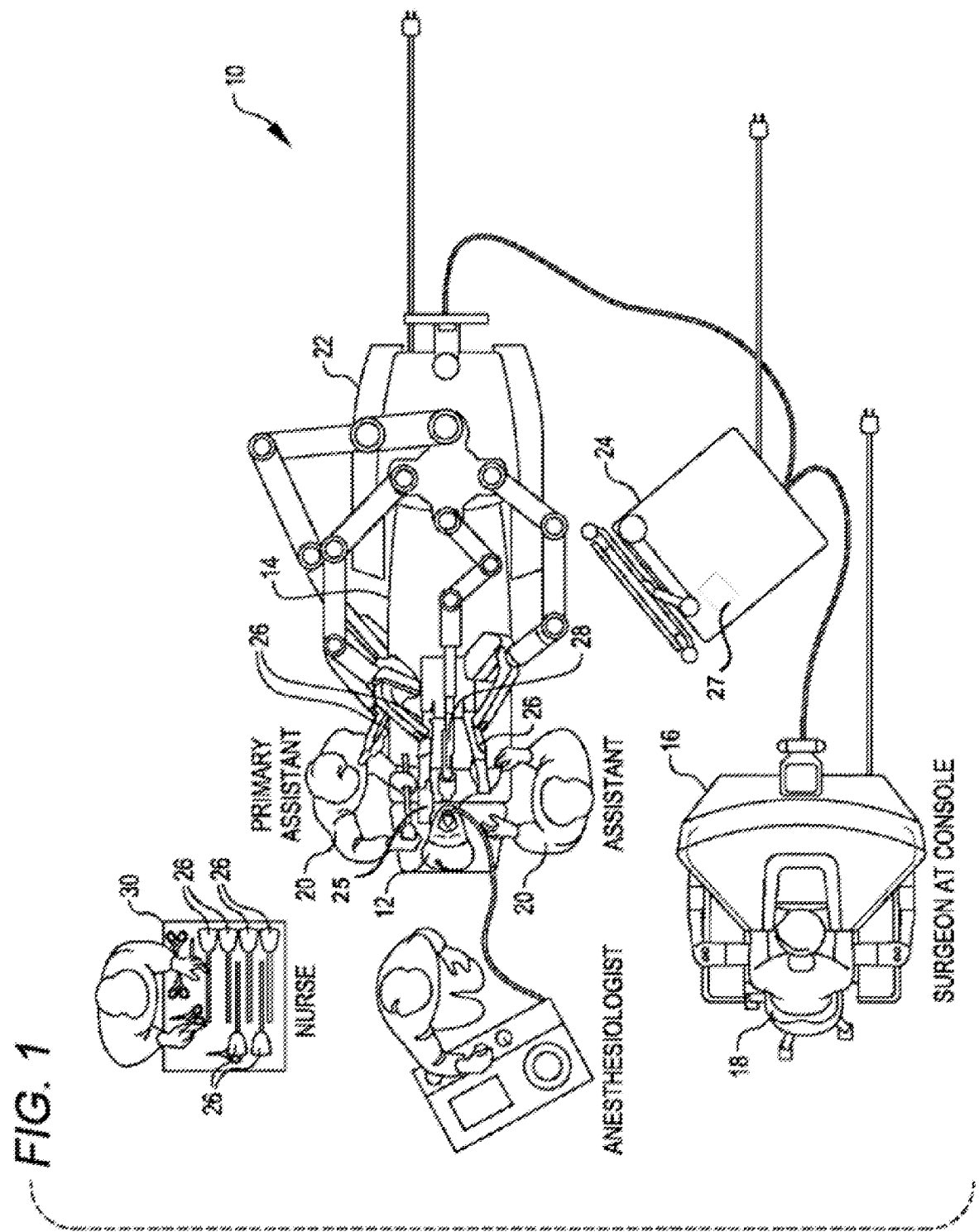
FIG. 1 is a plan view of a minimally invasive robotic surgery system being used to perform a surgery, in accordance with many embodiments.

Improved systems and methods related to clamping of body tissues are provided. The present invention relates to providing an indicator of whether clamping of grasped tissue is likely before attempting to clamp the tissue. The invention may be used in systems having jaw members for clamping a body tissue, particularly in surgical systems used in minimally invasive surgical applications. Typically, systems utilizing the claimed methods have jaws that grasp a body tissue at a low force and subsequently clamp the body tissue at a higher force. Grasping the body tissue at a low force allows a physician to manipulate and position the body tissue between the jaw members without causing damage to the tissue, while clamping at a higher clamping force allows the physician to perform various procedures, such as tissue cutting and sealing or stapling. While the various embodiments disclosed herein are primarily described with regard to surgical applications, these surgical applications are merely example applications, and the disclosed systems and methods can be used in other suitable applications, both inside and outside a human body, as well as in non-surgical applications.

In many embodiments, the two jaws comprise an articulated jaw that moves toward a stationary portion of the end effector. In such embodiments, the stationary portion of the end effector comprises the second jaw. In many embodiments, the system uses two independent mechanisms to articulate the jaws of the end effector. A first actuation mechanism provides a fast response/low force mode that varies the position of the articulated jaw between a closed (grasped) configuration and an open configuration. In many embodiments, the first actuation mechanism is back-drivable. For example, in the low force mode grasping mode the first actuation mechanism can be designed to provide 5 lbs of clamping force between the tips of the first and second jaw. A second actuation mechanism provides a high clamping force mode for clamping the body tissue between the jaws at the higher clamping force. Often, the second actuation mechanism is non-back-drivable. The second actuation mechanism converts a relatively weak force or torque (but with large displacement available) to a relatively high torque rotating the jaw of the end effector. The second actuation mechanism can be designed to provide, for example, 50 pounds of clamping force between the tips of the clamped jaws.

Typically, in applications using the claimed methods, a surgeon grasps a body tissue at the grasping force between the jaws of the surgical tool, then clamps the body tissue at the higher clamping force. Periodically, the jaws may fail to successfully clamp the tissue at the higher clamping force, which may potentially result in damage to the tissue due to the high clamping forces. For example, the jaws may clamp on the tissue but the jaw tips may be separated further than desired due to excess deflection, resulting in potential tissue damage. The jaws may fail to successfully clamp the tissue for a variety of reasons, including insufficient or excess tissue grasped between the jaws, including interference from an adjacent tissue, such as a bone, or slippage of the tissue from between the jaws. Therefore, it would be advantageous for a physician to be able to predict when clamping failure may occur before clamping, thereby avoiding any potential damage to the tissue. The described systems and methods provide an indication to the physician of a prediction of whether clamping of the body tissue will be successful. Clamping may be considered successful when the jaws are in the clamped position and the distance between the jaws is sufficient for performing a desired therapy, such as firing a staple through the clamped tissue.

The indication of whether clamping success is more likely than not may be based, in whole or in part, on the separation between the jaw members while grasping the tissue therebetween. Ideally, the methods include grasping a tissue at the grasping force, measuring and/or determining a separation between the jaw members, and providing an indication to the physician as to whether clamping of the grasped tissue is more likely than not. The methods may further include measuring or determining the relative stiffness of the grasped tissue. These systems and methods of the present invention are particularly beneficial when used in minimally invasive surgery applications. Additionally, the indication of clamping success or failure may further include predictions at multiple grip forces (e.g. sequentially higher forces), such that a user may grip with a force that is indicated as likely resulting in successful clamping. In some embodiments, this feature may be extended to consider the likelihood of clamping success or failure based on jaw positions during a continuously increasing grip force. The clamping force may also include a variable clamping force that is dependent on a relationship between jaw position and gripping force. For example, if the distance between jaws is greater than desired, such as may occur when an indication of likely clamping failure is indicated, a higher clamping force may be applied (e.g. by the user or automatically) and a second data point measured to determine an indication of a clamping prediction at the higher clamping force.

Minimally Invasive Robotic Surgery

Referring now to the drawings, in which like reference numerals represent like parts throughout the several views, FIG. 1 is a plan view illustration of an embodiment of the present invention. FIG. 1 illustrates a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot), and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. Tool assembly 26 includes end effector 25, the end effector having jaws for grasping and clamping the tissue. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the Surgeon 18 through the Surgeon's Console 16. Electronics Cart 24 includes a Processor 27 for measuring a separation parameter between the jaw members of the tool. The grasping separation parameter may be measured directly or indirectly. The separation may be measured directly by the processor from the actual jaw members or from images representing the positions of the jaw members, or from various sensors of the system. For example, a Hall-effect type sensor can be positioned near the anvil jaw pivot to measure the closure angle of the jaws. The Hall-effect type sensor can be placed in the staple cartridge (or in either jaw of a pair of jaws) and a magnet correspondingly positioned in the anvil jaw (or opposing jaw). The sensor can then sense the magnet's proximity to determine if the anvil jaw is sufficiently closed. In another example, a shape sensing optical fiber can be placed in the jaw so that the jaw angle can be sensed. In some embodiments, at least one jaw may be equipped with a depth gauge and the opposite jaw may be equipped with a sensor to measure the depth gauge. For example, the depth gauge may be a small retractable needle that can be deployed once tissue is grasped to measure the separation distance between jaws. The separation may also be measured indirectly by calculating the separation from the tool positional data, such as from positional data, or derivatives thereof, obtained by the PSM. The processor may also provide the indication as to whether clamping is more likely than not in response to the separation parameter. The indication may be determined according to a formula or algorithm or obtained from a predetermined table of values. The system 10 then communicates an indicator of the prediction to the physician on the Surgeon's Console 16.

Figure 2:
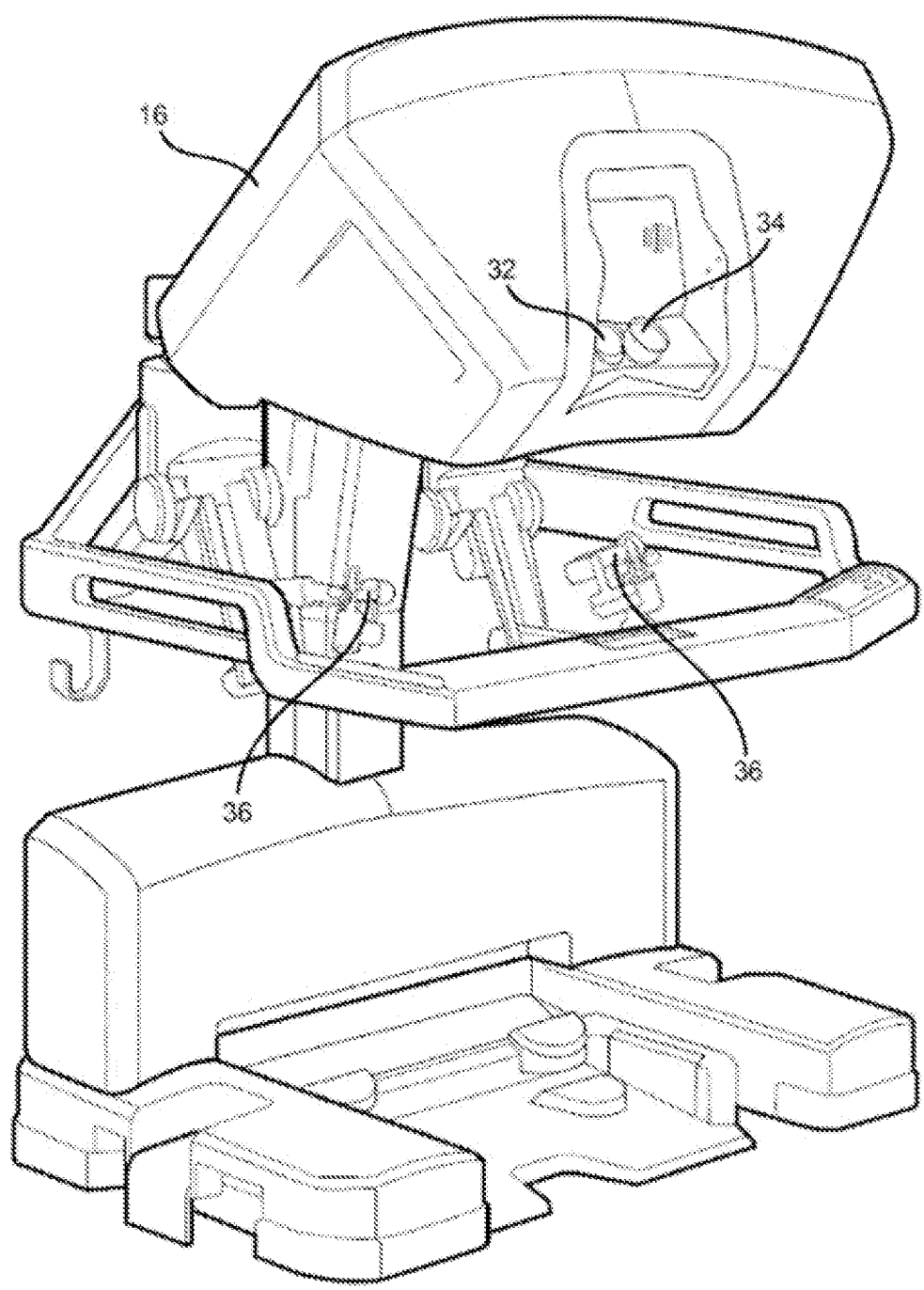
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 will provide the same degrees of freedom as their associated tools 26 (shown in FIG. 1) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures (i.e., operating from outside the sterile field).

Figure 3:
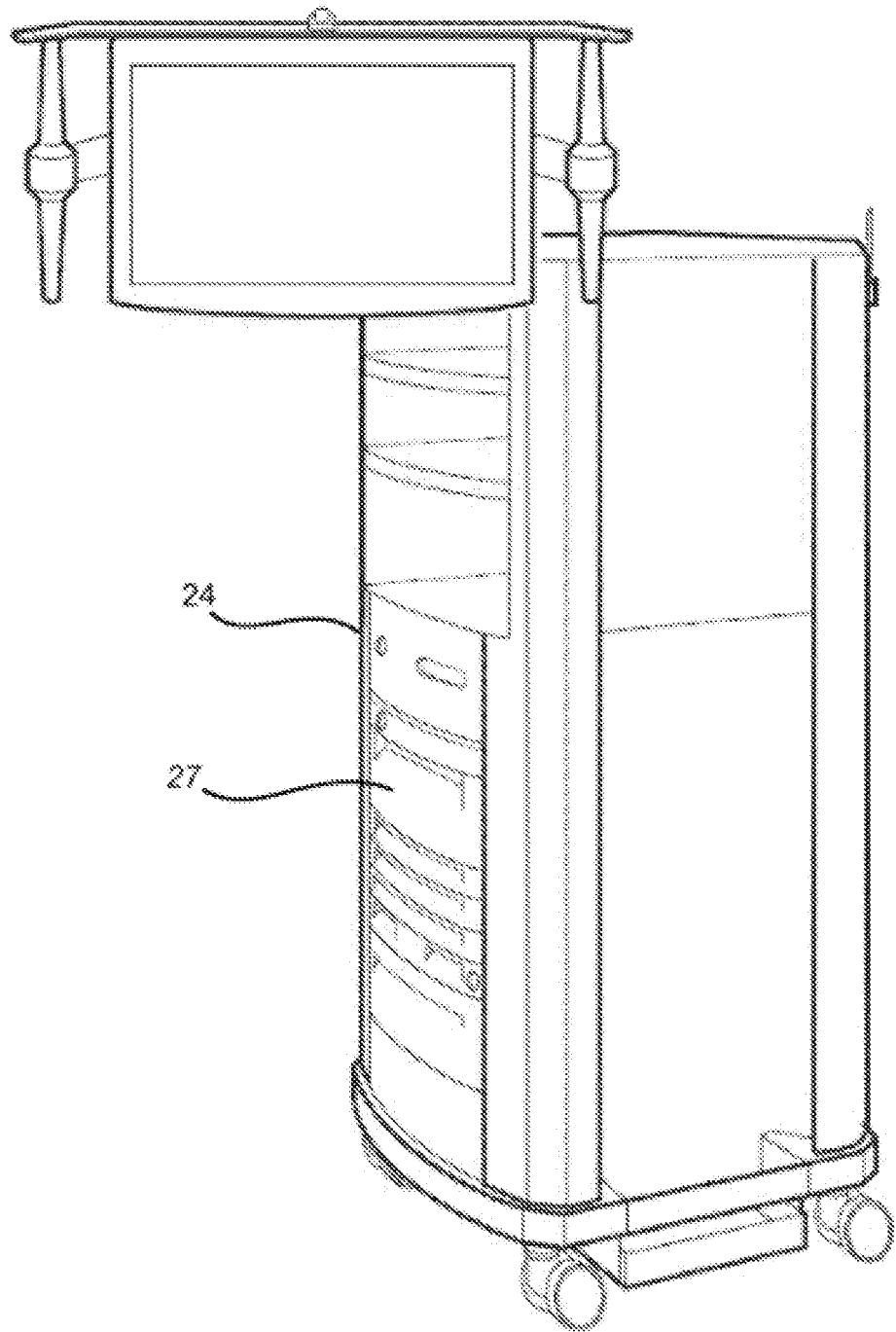
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include Processor 27 to measure and/or determine a separation parameter between jaw members of the tool and to determine a prediction of clamping success in response to the measured separation parameter. Processor 27 may also process captured images for subsequent display, such as to a Surgeon on the Surgeon's Console, or on any other suitable display located locally and/or remotely.

Figure 4:
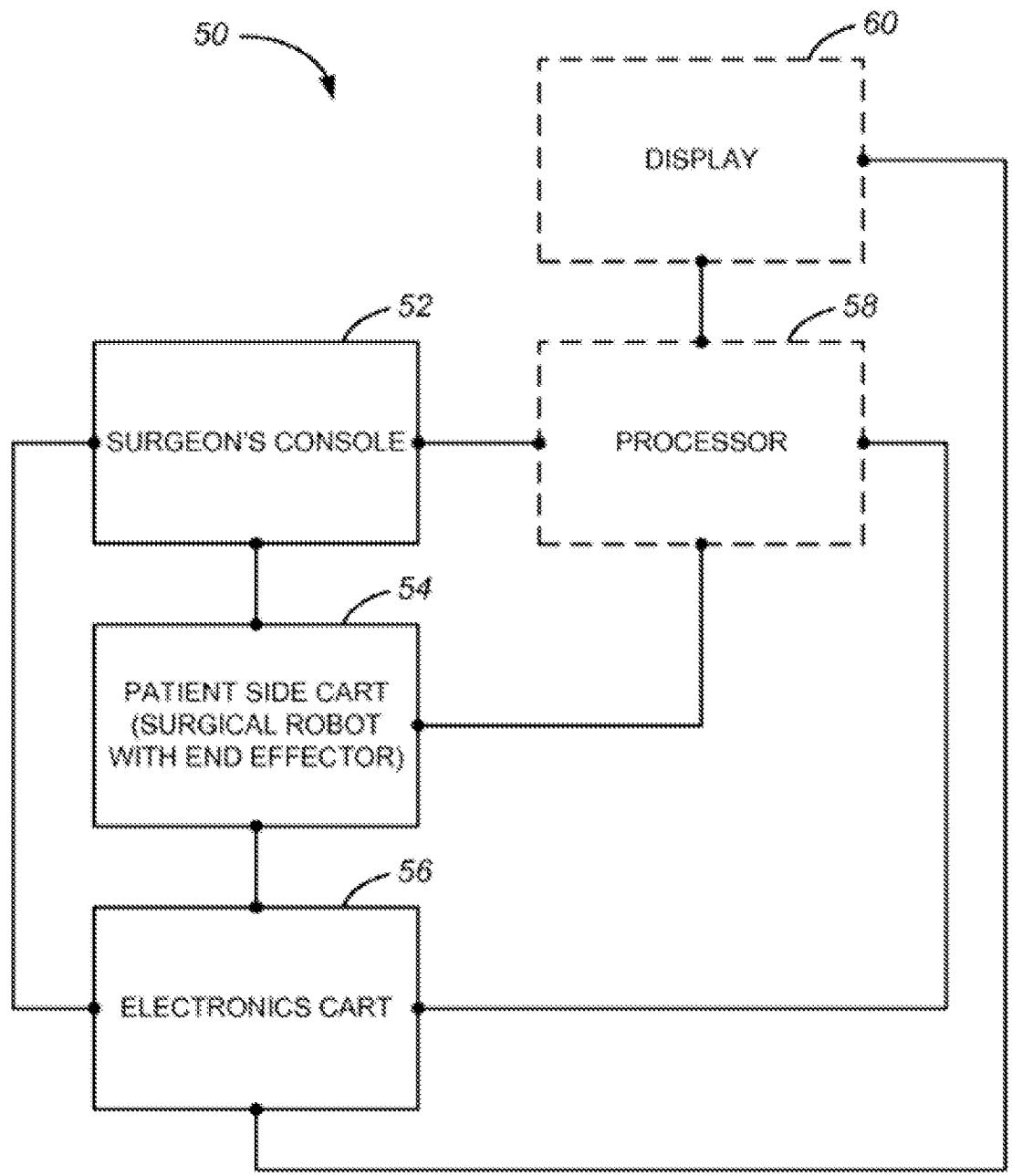
FIG. 4 diagrammatically illustrates a robotic surgery system, in accordance with many embodiments.

FIG. 4 diagrammatically illustrates a robotic surgery system 50 (such as MIRS system 10 of FIG. 1), in which the Processor 58 and Display 60 are depicted separately from Electronics Cart 56 and Surgeon's Console 52. As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. In preparation for clamping of a body tissue, the Surgeon can command the tool of the Patient Side Cart 54 to grasp a body tissue between jaw members of an end effector. In response to this command, Processor 58 can measure the separation parameter between the jaw members grasping the tissue and subsequently determine a clamping prediction based in whole or in part on the separation parameter. The determination of the clamping prediction may also include the grasping force, the desired clamping force and the desired distance between jaw members in the clamped configuration. The Processor 58 then commands Display 60 to display an indicator of the prediction to the Surgeon. In response, to the indicator the Surgeon may then safely proceed with clamping of the body tissue or may abort clamping and reposition the jaws until Display 60 indicates a prediction of clamping success.

Figure 5B:
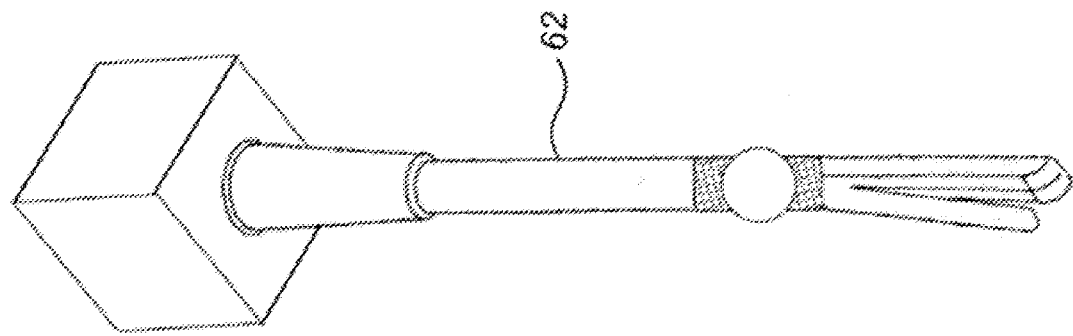
FIG. 5B is a front view of a robotic surgery tool.
Figure 5A:
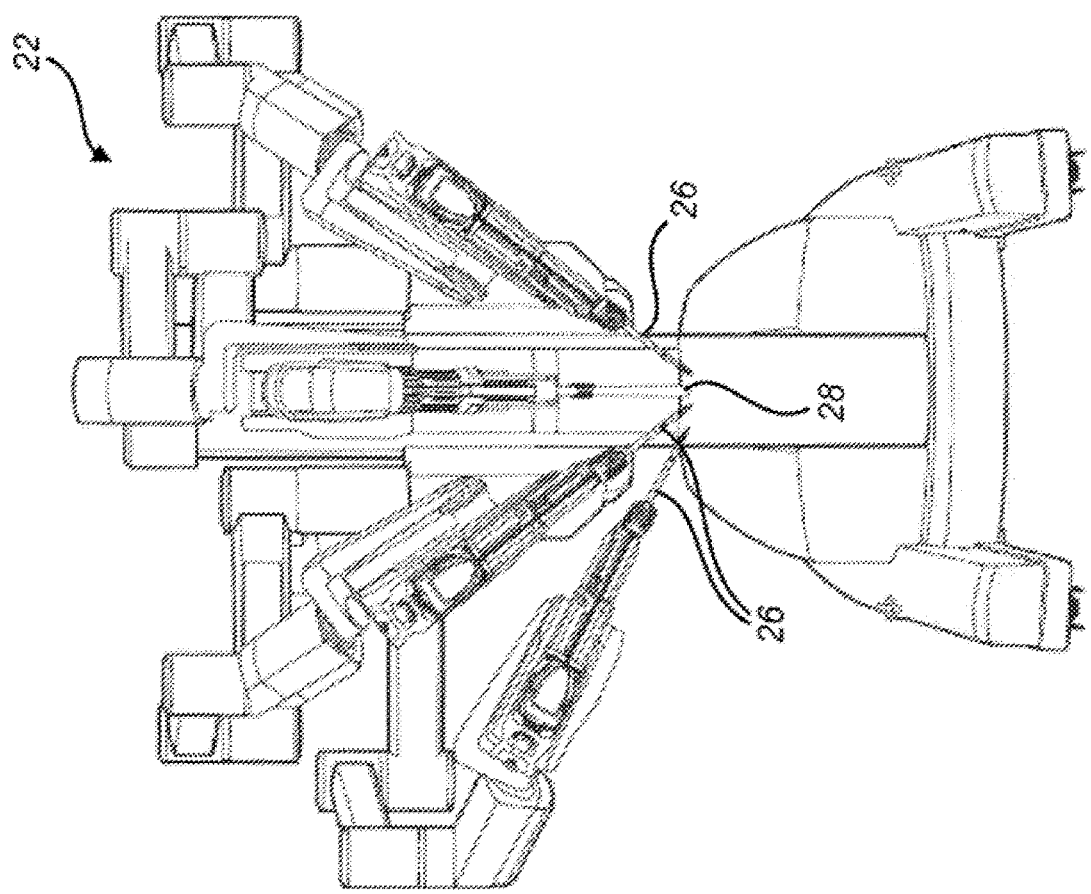
FIG. 5A is a front view of a patient side cart (surgical robot) of a robotic surgery system, in accordance with many embodiments.

FIGS. 5A and 5B show a Patient Side Cart 22 and a surgical tool 62, respectively. The surgical tool 62, one of the surgical tools 26, is an example of an end effector having a set of jaw members for grasping and clamping a body tissue. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical tools 26 when they are positioned within the field-of-view of the imaging device 28.

Tissue Grasping and Clamping with Independent Actuation Mechanisms

In many embodiments, two independent actuation mechanisms are used to control the articulation of an articulated jaw of an end effector. A first actuation mechanism can be used to provide a fast response/low force grasping mode, and a second actuation mechanism can be used to provide a high clamping force mode, the clamping force being greater than the grasping force. In many embodiments, the first actuation mechanism used to provide the fast response/low force articulation mode is back-drivable. In many embodiments, the second actuation mechanism used to provide the high clamping force articulation mode is non-back-drivable. Using independent actuation mechanisms may be beneficial in some surgical applications, for example, electrocautery sealing, stapling, etc., that may require multiple low force jaw placement clampings before a high force jaw clamping is used to carry out the surgical tool's task.

In many embodiments, actuation of the jaws in the fast response/low force grasping mode is provided by a cable actuation mechanism that includes a pair of pull cables. In many embodiments, a pulling motion of a first cable of the pair articulates the articulated jaw towards a closed (grasped) configuration and a pulling motion of a second cable of the pair articulates the articulated jaw towards an open (ungrasped) configuration. In many embodiments, the cable actuation mechanism is back-drivable.

In many embodiments, actuation of the jaws in the high clamping force mode is provided by a leadscrew actuation mechanism that includes a leadscrew driven cam. The driven cam interfaces with a mating cam surface on the articulated jaw so as to hold the articulated jaw in a closed (clamped) configuration when the leadscrew driven cam is at a first end of its range of motion. In addition, the driven cam does not constrain motion of the articulated jaw when the leadscrew driven cam is at a second end (opposite end) of its range of motion. In other words, the mating cam surfaces are arranged such that motion of the leadscrew driven cam in one direction will cause the articulated jaw to close, and motion of the leadscrew driven cam in the reverse direction will allow (but not force) the articulated jaw to open to a limit provided by the cam surfaces. Often, the leadscrew actuation mechanism is non-back-drivable. In many embodiments, the position of the jaw members of the end effector can be determined by the position of the cable actuation mechanism, or if driven by a leadscrew, the position of the leadscrew.

Figure 6A:
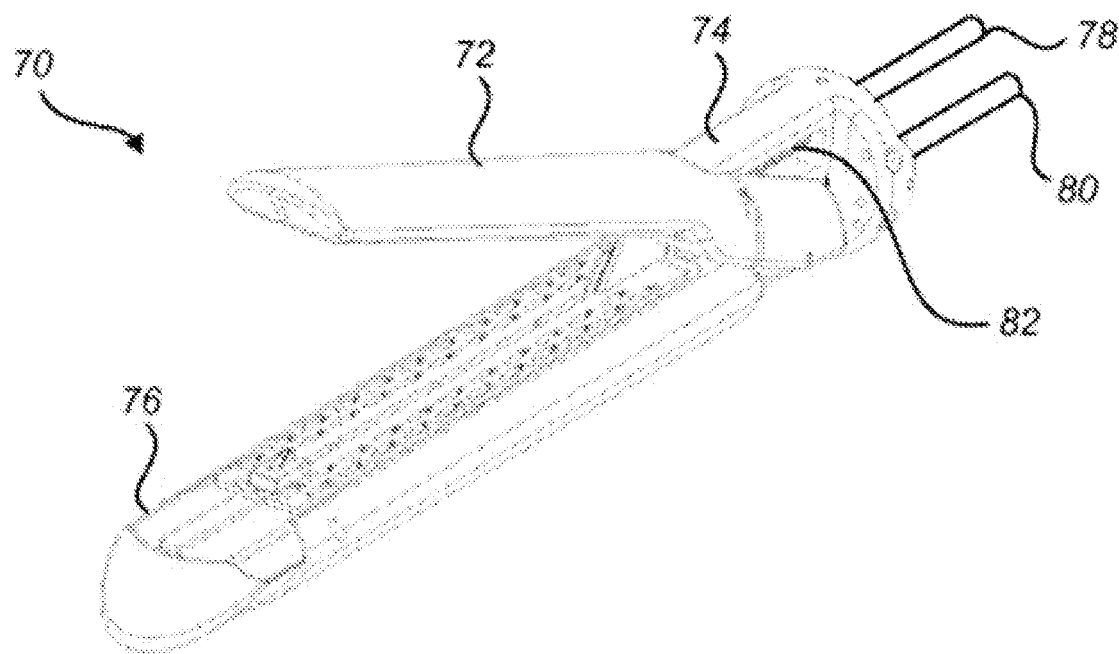
FIG. 6A is a perspective view of an end effector having an articulated jaw, in accordance with many embodiments.

FIG. 6A is a perspective view of an end effector 70 having a jaw 72 articulated by two independent actuation mechanisms, in accordance with many embodiments. The end effector 70 includes an end effector base 74, the articulated jaw 72, and a detachable stationary jaw 76. The end effector 70 is actuated via a first drive shaft 78, a second drive shaft 80, and two actuation cables (not shown). The first drive shaft 78 rotates a leadscrew 82 of a leadscrew actuation mechanism. The second drive shaft 80 rotates another leadscrew (not shown) of the detachable stationary jaw/staple cartridge reload 76.

In many embodiments, the first drive shaft 78 and/or the second drive shaft 80 are driven by drive features located in a proximal tool chassis to which the end effector 70 is coupled with via an instrument shaft. In many embodiments, the proximal tool chassis is configured to be releasably mountable to a robotic tool manipulator. In many embodiments, the first drive shaft 78 and the second drive shaft 80 are actuated via respective drive features located in the proximal tool chassis. In many embodiments, such drive features are driven by an actuator or motor system that is located in the proximal tool chassis.

Figure 6B:
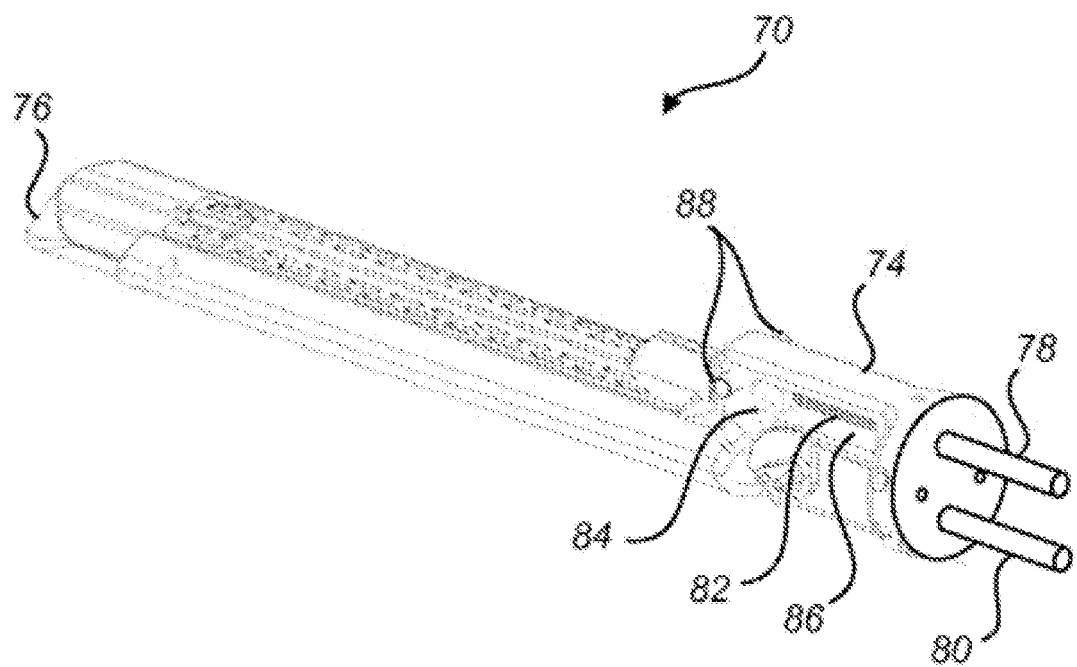
FIG. 6B is a perspective view of the end effector of FIG. 6A (with the articulated jaw removed to better illustrate leadscrew actuation mechanism components), in accordance with many embodiments.

FIG. 6B is a perspective view of the end effector 70 of FIG. 6A (with the articulated jaw 72 removed to better illustrate components of the leadscrew actuation mechanism), in accordance with many embodiments. The leadscrew 82 is mounted for rotation relative to the end effector base 74. A leadscrew driven cam 84 is coupled with the leadscrew 82 so that selective rotation of the leadscrew 82 can be used to selectively translate the leadscrew driven cam 84 along a cam slot 86 in the end effector base 74. The end effector 70 includes a pivot pin 88 that is used to rotationally couple the articulated jaw 72 with the end effector base 74.

FIGS. 7A through 10 illustrate the actuation mechanisms by which an end effector grasps a body tissue between its jaws in the low force grasping mode and clamps the body tissue grasped between its jaws with a higher clamping force.

Figure 7A:
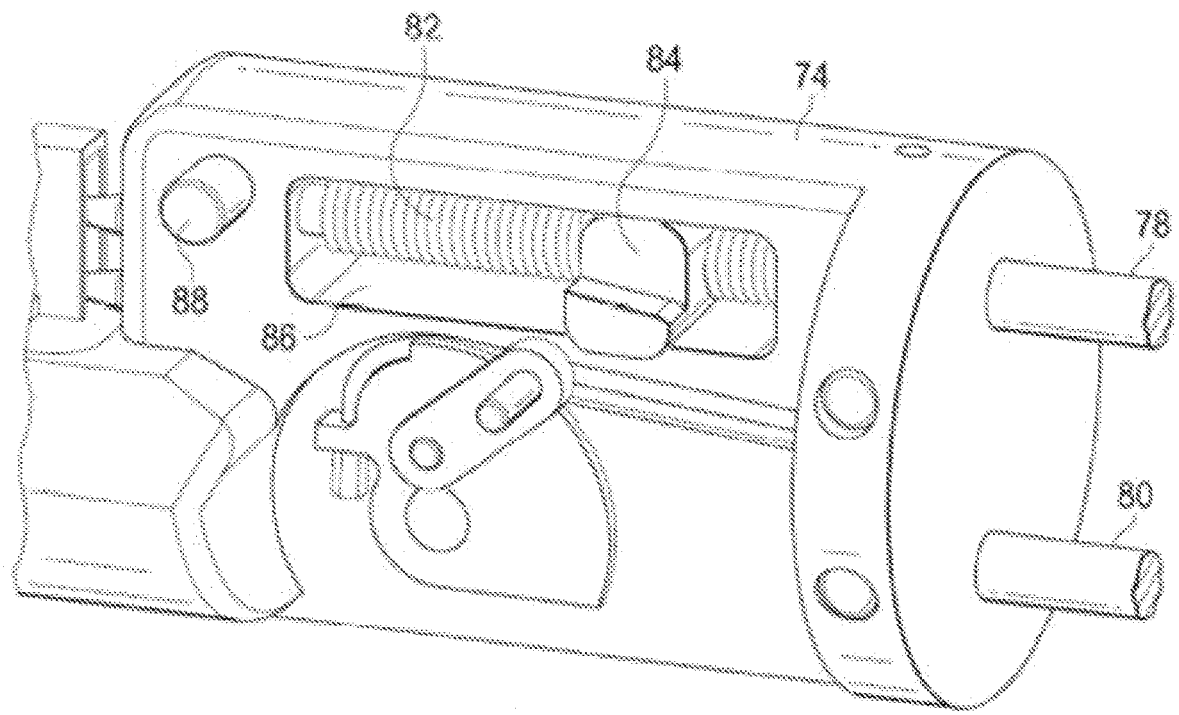
FIGS. 7A and 7B illustrate components of a leadscrew actuation mechanism, in accordance with many embodiments.
Figure 7B:
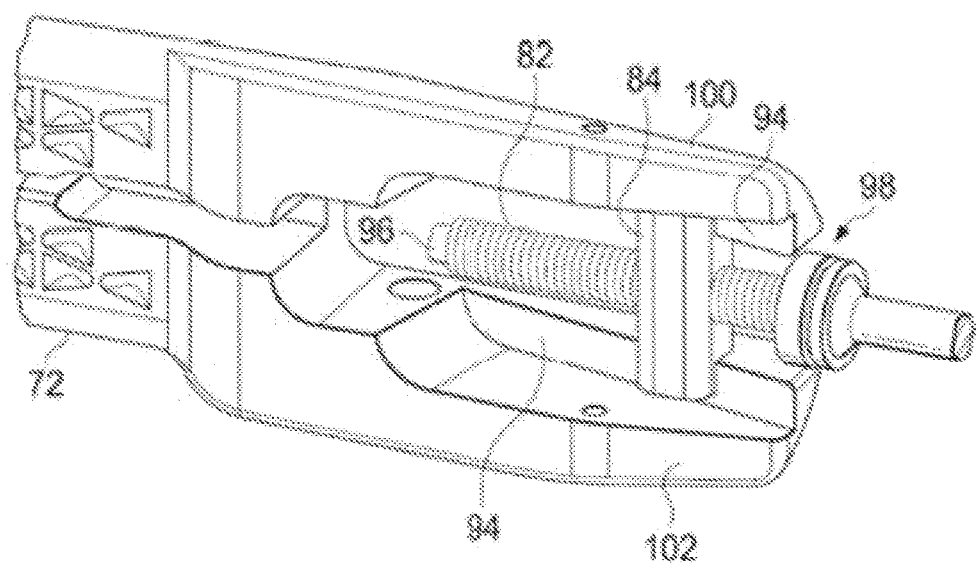
Figure 8A:
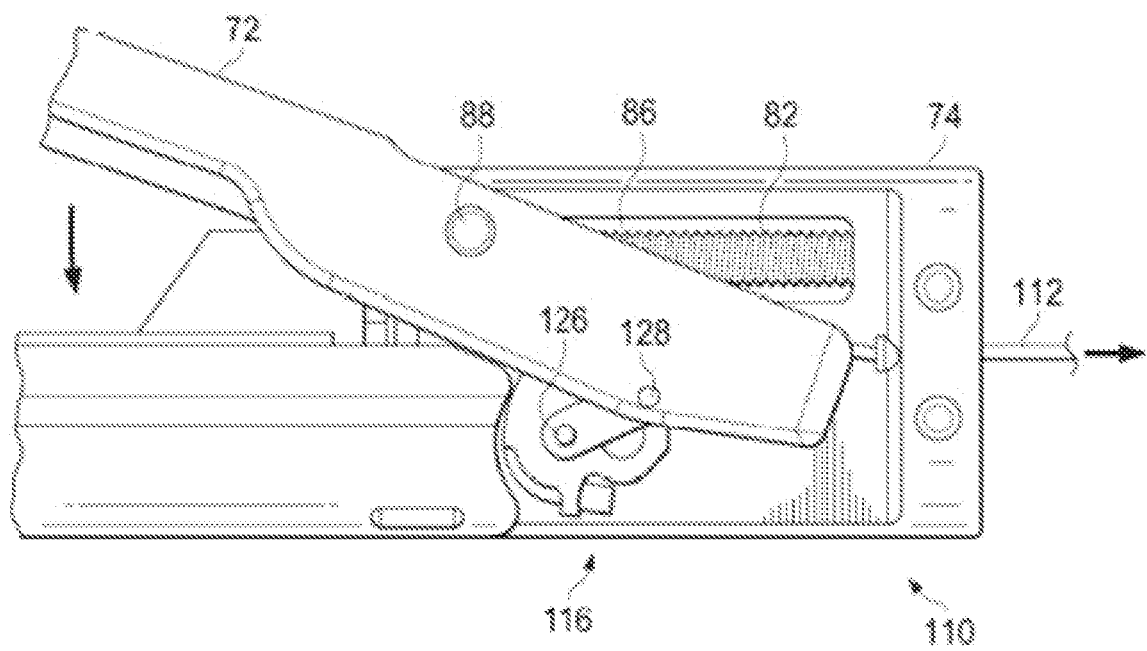
FIG. 8A illustrates components of a cable-driven actuation mechanism, in accordance with many embodiments.
Figure 8B:
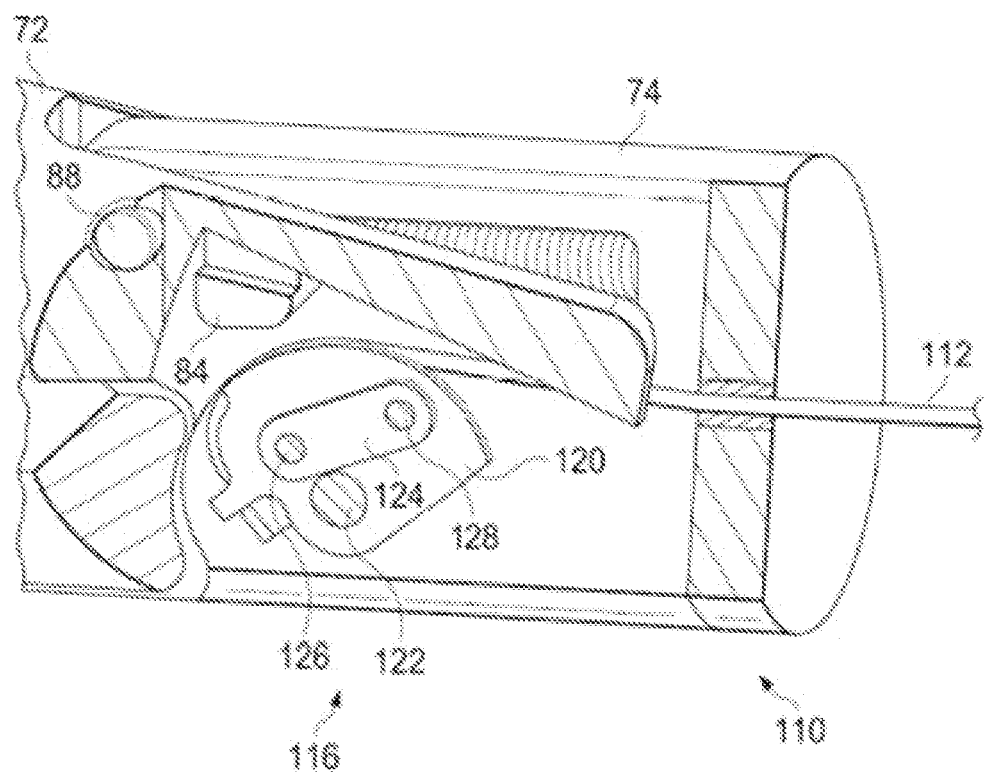
FIG. 8B is a perspective view of the end effector of FIG. 8A with a portion of the articulated jaw removed to show cable-driven actuation mechanism components disposed behind the articulated jaw used to articulate the jaw towards a closed configuration, in accordance with many embodiments.
Figure 8C:
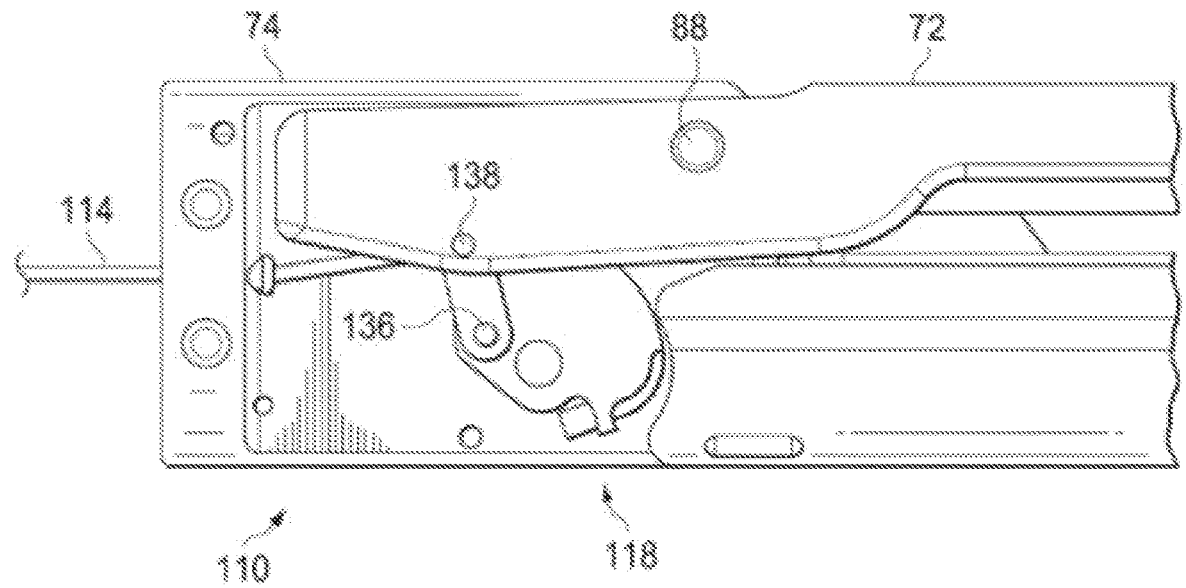
FIGS. 8C through 8F illustrate opposite side components of the cable-driven actuation mechanism of FIG. 8A used to articulate the jaw towards an open configuration.
Figure 8D:
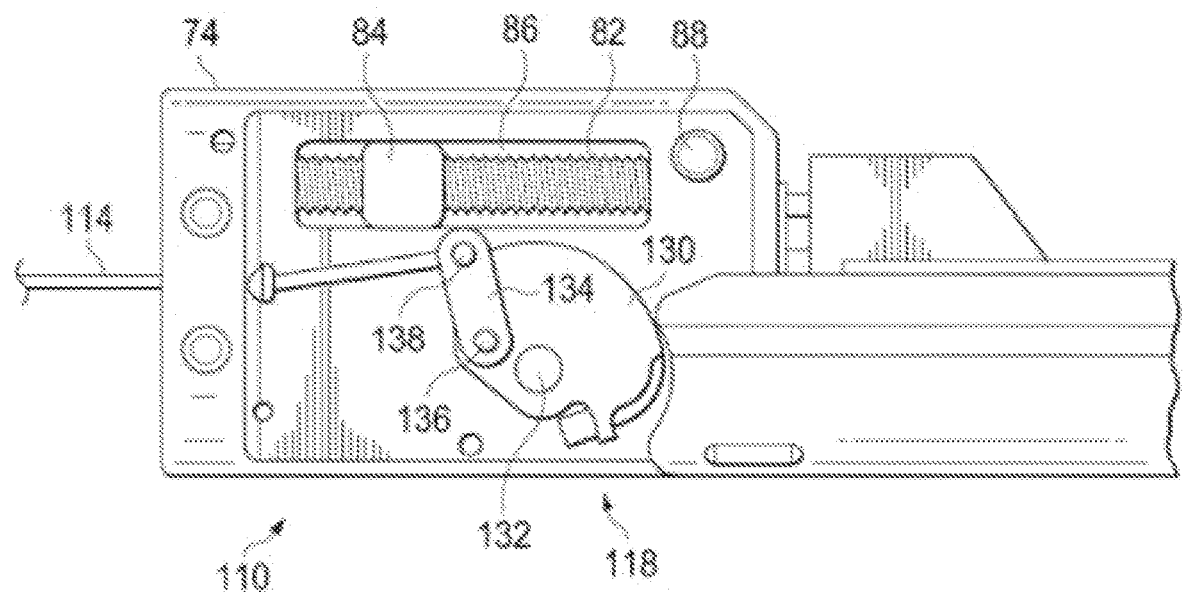
Figure 8E:
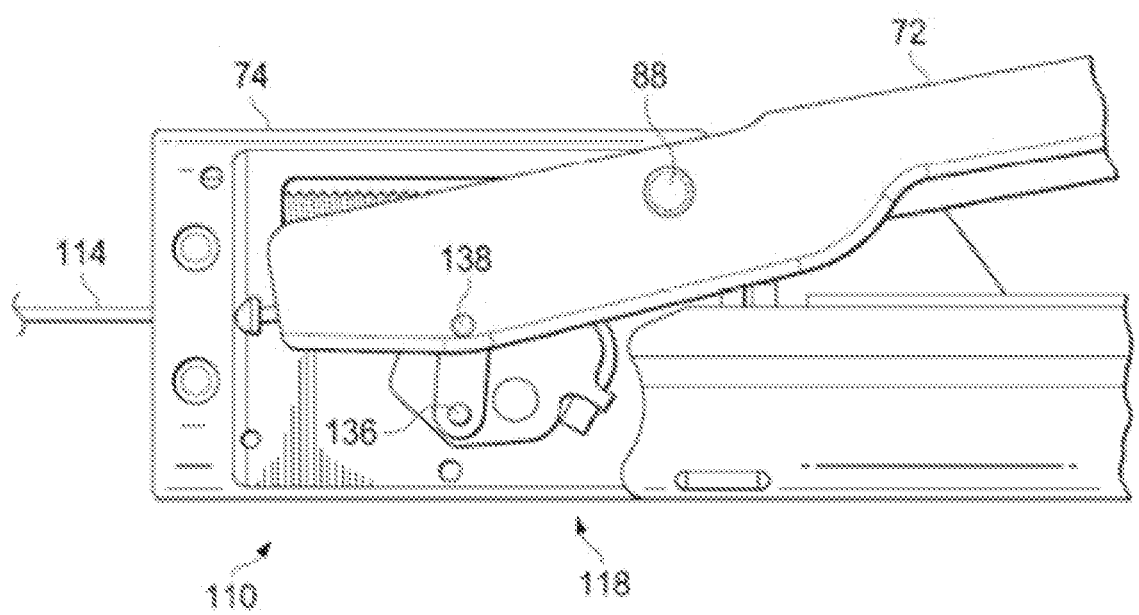
Figure 8F:
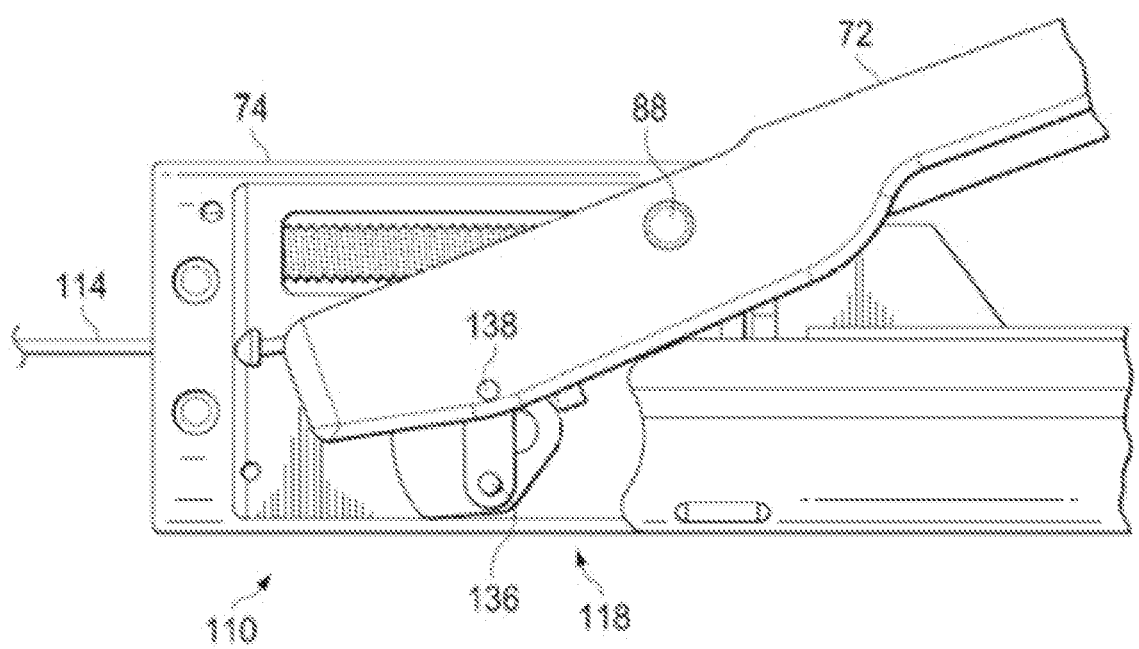

FIGS. 7A and 7B illustrate the leadscrew actuation mechanism of FIGS. 6A and 6B. The leadscrew 82 has a distal journal surface 96 and a proximal journal surface that interfaces with a proximal bearing 98. In many embodiments, the distal journal surface 96 is received within a cylindrical receptacle located at the distal end of the cam slot 86. Such a distal support for the leadscrew 82 can be configured to keep the leadscrew 82 from swinging excessively, and with relatively large clearance(s) between the distal journal surface 96 and the cylindrical receptacle. The proximal bearing 98 is supported by the end effector base 74 so as to support the proximal end of the leadscrew 82. The proximal bearing 98 can be a ball bearing, which may help to reduce friction and wear. A distal bearing (not shown) can be supported by the end effector base 74 so as to support the distal end of the leadscrew 82, and the distal bearing can be a ball bearing. The leadscrew driven cam 84 includes a threaded bore configured to mate with the external threads of the leadscrew 82. The leadscrew driven cam 84 includes top and bottom surfaces configured to interact with corresponding top and bottom surfaces of the cam slot 86. The interaction between leadscrew driven cam 84 and the cam slot 86 prevents the leadscrew driven cam 84 from rotating relative to the cam slot 86, which causes the leadscrew driven cam 84 to translate along the cam slot 86 in response to rotation of the leadscrew.

The articulated jaw 72 includes mating cam surfaces 94 that are configured so that the position of the leadscrew driven cam 84 along the cam slot 86 determines the extent to which the rotational motion of the articulated jaw 72 around the pivot pin 88 is constrained by the leadscrew driven cam 84. The articulated jaw 72 includes a first proximal side 100 and a second proximal side 102 that are separated by a central slot. The first and second proximal sides are disposed on opposing sides of the end effector base 74 when the articulated jaw 72 is coupled with the end effector base 74 via the pivot pin 88. Each of the first and second proximal sides 100, 102 includes a recessed area defining a mating cam surface 94 and providing clearance between the leadscrew driven cam 84 and the proximal sides 100, 102. When the leadscrew driven cam 84 is positioned at or near the proximal end of the cam slot 86 (near its position illustrated in FIGS. 7A and 7B), contact between the leadscrew driven cam 84 and the mating cam surfaces 94 of the articulated jaw 72 hold the articulated jaw in a clamped configuration. When the leadscrew driven cam 84 is positioned at the distal end of the cam slot 86, the rotational position of the articulated jaw around the pivot pin 88 is unconstrained by the leadscrew driven cam 84 for a range of rotational positions between a clamped configuration (where there is a gap between the leadscrew driven cam 84 and the mating cam surfaces 94 of the articulated jaw 72) and an open configuration (where there may or may not be a gap between the leadscrew driven cam 84 and the mating cam surfaces 94 of the articulated jaw 72). For positions of the leadscrew driven cam 84 in between the proximal and distal ends of the cam slot 86, the range of unconstrained motion can vary according to the cam surfaces used.

The use of a recess in each of the proximal sides 100, 102 to define the mating cam surfaces 94 of the articulated jaw 72 provides a number of benefits. For example, the use of recesses as opposed to traverse slots that extend through the proximal sides provides a continuous outside surface to the proximal sides 100, 102 of the articulated jaw, which is less likely to snag on patient tissue than would a traverse slot opening. The absence of traverse slots also helps to stiffen the proximal sides 100, 102 as compared to proximal sides with traverse slots, and therefore provides increased clamping stiffness. Such proximal sides 100, 102 may have increased stiffness in two planes, which may help maintain alignment of the articulated jaw 72 in the presences of external forces. Such increased stiffness in two planes may be beneficial in some surgical applications, for example, in tissue stapling where it is beneficial to maintain alignment between the staples and anvil pockets that form the staples. Further, the use of recesses instead of traverse slots also provides an actuation mechanism that is less likely to be jammed by extraneous material as compared to one having proximal sides with open traverse slots.

The leadscrew actuation mechanism can be configured to provide a desired clamping force between the articulated jaw and an opposing jaw of the end effector. For example, in many embodiments, the leadscrew actuation mechanism is configured to provide at least 20 lbs of clamping force at the tip of the articulated jaw 72 (approximately 2 inches from the pivot pin 88). In many embodiments, the leadscrew actuation mechanism is configured to provide at least 50 lbs of clamping force at the tip of the articulated jaw 72. In many embodiments, to produce 50 lbs of clamping force at the tip of the articulated jaw 72, the input torque to the leadscrew 82 is approximately 0.1 Newton meter and the leadscrew 82 has approximately 30 turns.

The leadscrew actuation mechanism can be fabricated using available materials and components. For example, many components of the leadscrew actuation mechanism can be fabricated from an available stainless steel(s). The leadscrew driven cam 84 can be coated (e.g., TiN) to reduce friction against the surfaces it rubs against (e.g., leadscrew 82; end effector base 74; proximal sides 100, 102 of the articulated jaw 72). Stranded cables can be used to drive the first actuation mechanism.

FIGS. 8A through 8F illustrate components of a cable actuation mechanism 110, in accordance with many embodiments. As described above, the leadscrew driven cam 84 can be positioned at the distal end of the cam slot 86 (i.e., near the pivot pin 88). For such a distal position of the leadscrew driven cam 84, as discussed above, the rotational position of the articulated jaw 72 about the pivot pin 88 is unconstrained for a range of rotational positions of the articulated jaw 72. Accordingly, the rotational position of the articulated jaw 72 about the pivot pin 88 can be controlled by the cable actuation mechanism 110. The cable actuation mechanism 110 is operable to vary the rotational position of the articulated jaw between the closed configuration and the open configuration. The cable actuation mechanism 110 includes a pair of pull cables 112, 114. The cable actuation mechanism 110 also includes a first linkage 116 that is used to rotate the articulated jaw 72 about the pivot pin 88 towards the closed configuration, and an analogous second linkage 118 that is used to rotate the articulated jaw 72 about the pivot pin 88 towards the open configuration. The first linkage 116 (shown in FIGS. 8A and 8B) includes a rotary link 120 that is mounted for rotation relative to the end effector base 74 via a pivot pin 122. A connecting link 124 couples the rotary link 120 to the articulated jaw 72 via a pivot pin 126 and a pivot pin 128. The first linkage 116 is articulated via a pulling motion of the pull cable 112. In operation, a pulling motion of the pull cable 112 rotates the rotary link 120 in a clockwise direction about the pivot pin 122. The resulting motion of the connecting link 124 rotates the articulated jaw 72 in a counter-clockwise direction about the pivot pin 88 towards the closed configuration.

The second linkage 118 (shown in FIGS. 8C through 8F) of the cable actuation mechanism 110 includes analogous components to the first linkage 116, for example, a rotary link 130 mounted for rotation relative to the end effector base 74 via a pivot pin 132, and a connecting link 134 that couples the rotary link 130 to the articulated jaw 72 via two pivot pins 136, 138. The second linkage 118 is articulated via a pulling motion of the pull cable 114. The second linkage 118 is configured such that a pulling motion of the pull cable 114 rotates the articulated jaw 72 about the pivot pin 88 towards the open configuration. In many embodiments, the pivot pin 136 between the connecting link 134 and the rotary link 130 of the second linkage 118 is 180 degrees out of phase with the pivot pin 126 between the connecting link 124 and the rotary link 120 of the first linkage 116. Coordinated pulling and extension of the pull cables 112, 114 of the cable actuation mechanism 110 is used to articulate the articulated jaw 72 between the open and closed configurations. In order to best provide equal and opposite cable motion (and thereby maintain cable tension in a capstan-driven system described below), a common rotational axis for the pivot pins 122, 132 is configured to lie on a plane that contains the rotational axes for pivot pins 128, 138 when the articulated jaw 72 is closed (or nearly closed) and again when the when the articulated jaw 72 is open (or nearly open). The connecting links 124, 134 are assembled symmetrically opposite about this same plane for the first and second linkages 116, 118. The distance between the pivot pins 122, 126 and between the pivot pins 132, 136 is the same for both the first and second linkages 116, 118, and the distance between the pivot pins 126, 128 and between the pivot pins 136, 138 is the same for both the first and second linkages 116, 118.

Figure 9A:
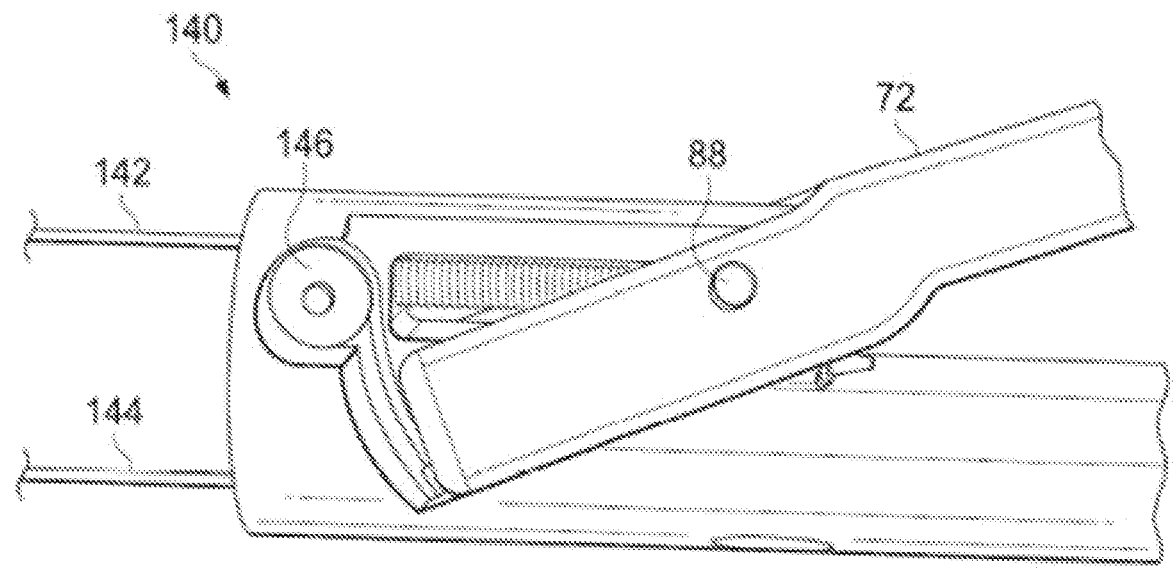
FIG. 9A is a perspective view illustrating a cable actuation mechanism, showing a cable used to articulate the jaw towards a closed configuration, in accordance with many embodiments.
Figure 9B:
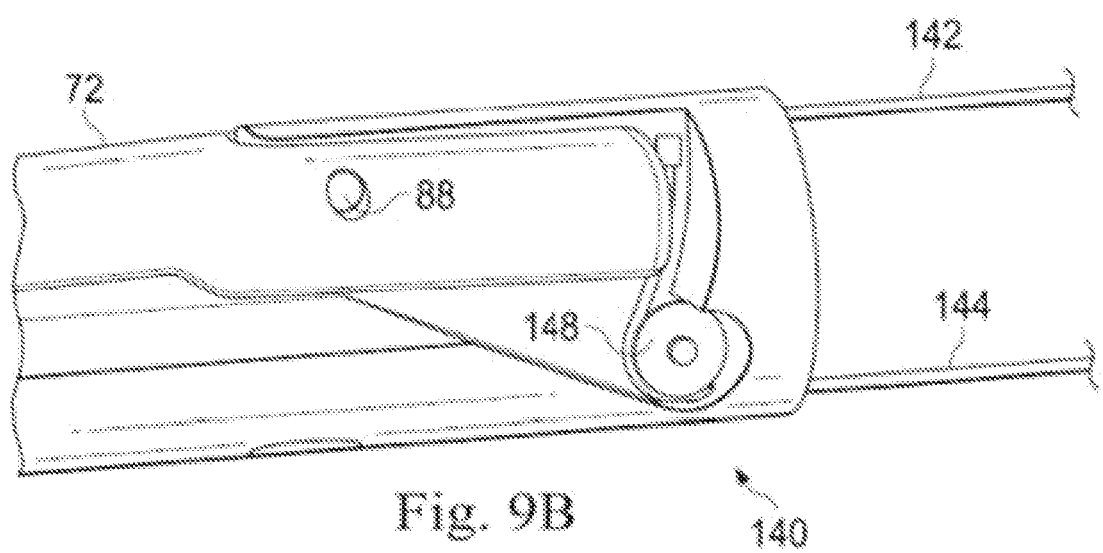
FIG. 9B is a perspective view illustrating the cable actuation mechanism of FIG. 9A, showing a cable used to articulate the jaw towards an open configuration.

FIGS. 9A and 9B illustrate an articulation of the articulated jaw 72 via another cable actuation mechanism 140, in accordance with many embodiments. In embodiment 140 of the cable actuation mechanism, a first pull cable 142 and a second pull cable 144 are directly coupled with the proximal end of the articulated jaw 72. The first pull cable 142 wraps around a first pulley 146 so that a pulling motion of the first pull cable 142 rotates the articulated jaw 72 about the pivot pin 88 towards the clamped configuration. The second pull cable 144 wraps around a second pulley 148 so that a pulling motion of the second pull cable 144 rotates the articulated jaw 72 about the pivot pin 88 towards the open configuration. Accordingly, coordinated pulling and extension of the first and second pull cables of the cable actuation mechanism 140 is used to articulate the articulated jaw 72 between the open and clamped configurations. In order to best provide equal and opposite cable motion (and thereby maintain cable tension in the capstan-driven system described below), the radius of the arc prescribed by cable 142 about the pivot 88 is substantially the same as the radius prescribed by cable 144 about the pivot 88.

In many embodiments, the cable (i.e., low force) actuation mechanism comprises a pair of pull cables that are actuated via an actuation feature disposed in a proximal tool chassis. The proximal tool chassis can be configured to be releasably mountable to a robotic tool manipulator having a drive mechanism that operatively couples with the actuation feature. For example, the pair of pull cables can be wrapped around a capstan located in the proximal tool chassis. The capstan can be operatively coupled with a capstan drive servo motor of the robotic tool manipulator when the proximal tool chassis is mounted to the robotic tool manipulator. Selective rotation of the capstan drive motor can be used to produce a corresponding rotation of the capstan. Rotation of the capstan can be used to produce a coordinated extension and retraction of the pull cables. As discussed above, coordinated actuation of the pull cables can be used to produce a corresponding articulation of the articulated jaw of the end effector.

In many embodiments, the fast response/low force mode is provided by a cable actuation mechanism that is back-drivable. For example, an external force applied to the articulated jaw can be used to rotate the articulated jaw towards the clamped configuration and back-drive the cable actuation mechanism. With a cable actuation mechanism that comprises a pair of pull cables wrapped around a capstan, an external force that rotates the articulated jaw towards the closed configuration produces an increase in tension in one of the pull cables and a decrease in tension in the other pull cable, thereby causing the capstan to rotate in response. As is known, such a cable driven system can be configured to have sufficient efficiency for back-drivability. Likewise, an external force applied to the articulated jaw can be used to rotate the articulated jaw towards the open configuration and back-drive the cable actuation mechanism. As discussed above, a back-drivable fast response/low force actuation mechanism provides a number of benefits.

Alternate mechanisms can be used to provide a fast response/low force articulation mode. For example, an actuation mechanism comprising push/pull rods can be used.

Figure 10:
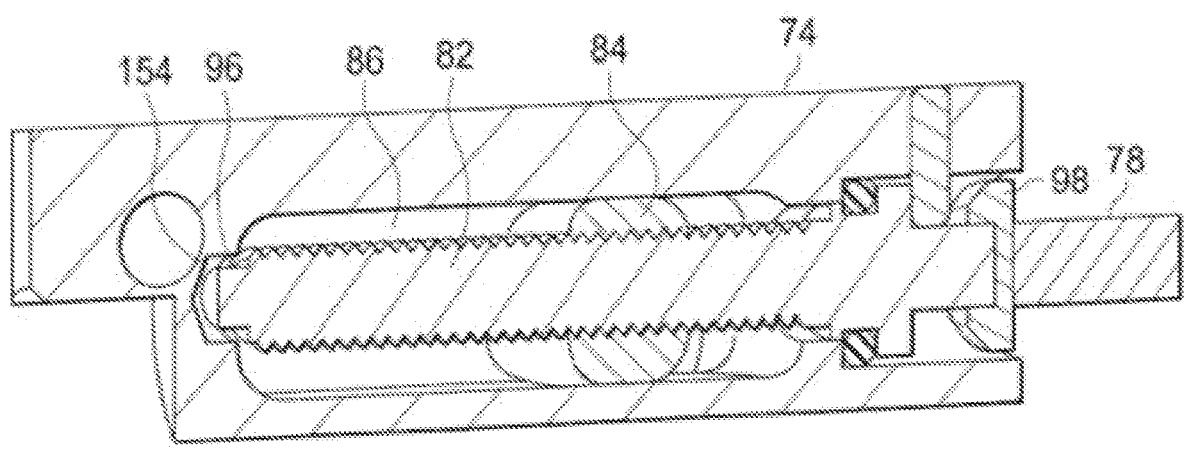
FIG. 10 is a cross-sectional view illustrating components of a leadscrew actuation mechanism, in accordance with many embodiments.

FIG. 10 is a cross-sectional view illustrating components of the above discussed leadscrew actuation mechanism. The illustrated components include the leadscrew 82, the leadscrew driven cam 84, the cam slot 86 in the end effector base 74, the distal journal surface 96, the cylindrical receptacle 154 in the end effector base, and the proximal bearing 98 supported by the end effector base 74.

Figure 11:
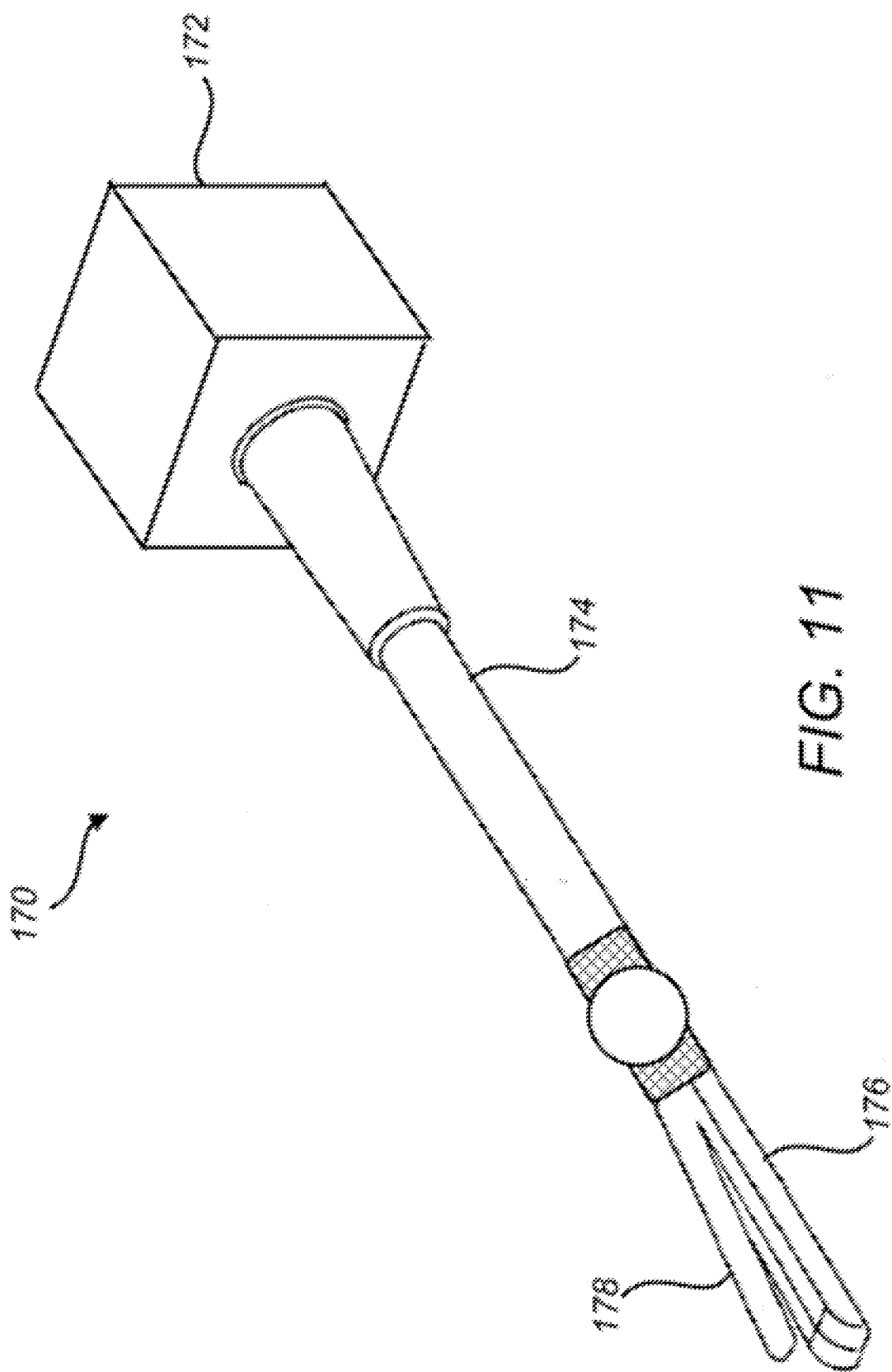
FIG. 11 is a simplified diagrammatic illustration of a tool assembly, in accordance with many embodiments.

FIG. 11 is a simplified perspective view diagrammatic illustration of a tool assembly 170, in accordance with many embodiments. The tool assembly 170 includes a proximal actuation mechanism 172, an elongate shaft 174 having a proximal end and a distal end, a tool body 176 disposed at the distal end of the shaft, a jaw 178 movable relative to the tool body 176 between a clamped configuration and an open configuration, a first actuation mechanism coupled with the jaw, and a second actuation mechanism coupled with the jaw. The first actuation mechanism is operable to vary the position of the jaw relative to the tool body between the clamped configuration and the open configuration. The second actuation mechanism has a first configuration where the jaw is held in the clamped configuration and a second configuration where the position of the jaw relative to the tool body is unconstrained by the second actuation mechanism. The first actuation mechanism is operatively coupled with the proximal actuation mechanism. In many embodiments, the first actuation mechanism comprises a pair of pull cables that are actuated by the proximal actuation mechanism. The second actuation mechanism is operatively coupled with the proximal actuation mechanism. In many embodiments, the second actuation mechanism includes a leadscrew driven cam located in the tool body that is driven by the proximal actuation mechanism via a drive shaft extending through the elongate shaft 174 from the proximal actuation mechanism. Although tool assembly 170 has been described as having a first and second actuation mechanism, in some embodiments tool assembly 170 could be constructed with a single actuation mechanism driven with a variable force motor such that the tool could both grasp body tissue with a relatively low force and subsequently clamp the grasped body tissue with a higher clamping force with the single actuation mechanism.

The tool assembly 170 can be configured for use in a variety of applications. For example, the tool assembly 170 can be configured as a hand held device with manual and/or automated actuation used in the proximal actuation mechanism. The tool assembly 170 can also be configured for use in surgical applications, for example, electrocautery sealing, stapling, etc. The tool assembly 170 can have applications beyond minimally invasive robotic surgery, for example, non-robotic minimally invasive surgery, non-minimally invasive robotic surgery, non-robotic non-minimally invasive surgery, as well as other applications where the use of the disclosed redundant jaw actuation would be beneficial.

Figure 12:
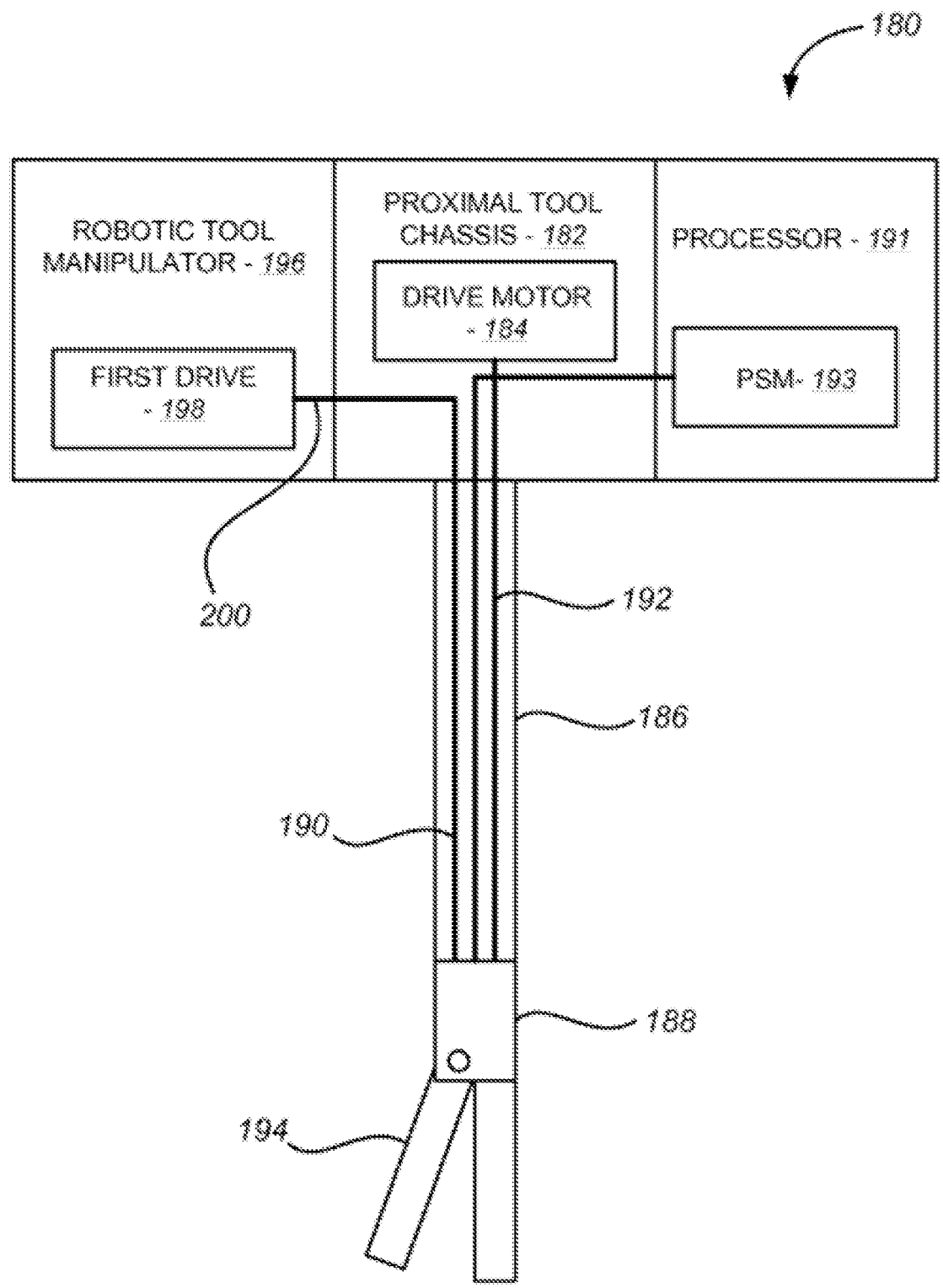
FIG. 12 is a simplified diagrammatic illustration of a robotic tool mounted to a robotic tool manipulator, in accordance with many embodiments.

Redundant jaw actuation can be used to articulate a jaw of a robotic tool end effector. For example, FIG. 12 schematically illustrates a robotic tool 180 employing redundant jaw actuation. The robotic tool 180 includes a proximal tool chassis 182, a drive motor 184, an instrument shaft 186, a distal end effector 188, a first actuation mechanism portion 190, and a second actuation mechanism 192. The distal end effector 188 comprises an articulated jaw 194. The proximal tool chassis 182 is releasably mountable to a robotic tool manipulator 196 having a first drive 198, and a first actuation mechanism portion 200 that operatively couples with the first actuation mechanism portion 190 of the robotic tool 180 when the proximal tool chassis 182 is mounted to the robotic tool manipulator 196. The instrument shaft 186 has a proximal end adjacent the tool chassis 182, and a distal end adjacent the end effector 188. The first actuation mechanism (comprising portion 200 and portion 190) couples the first drive 198 to the articulated jaw 194 when the tool chassis 182 is mounted to the tool manipulator 196 so as to articulate the end effector 188 between an open configuration and a closed configuration. The second actuation mechanism 192 couples the drive motor 184 to the articulated jaw 194 so as to articulate the end effector into the clamped/closed configuration from the open configuration. The first actuation mechanism can be a cable actuation mechanism, for example, an above discussed cable actuation mechanism that provides the fast response/low force mode. In many embodiments, the first actuation mechanism is back-drivable. The second actuation mechanism can include a drive shaft that couples the drive motor 184 with a leadscrew actuation mechanism, for example, an above discussed leadscrew actuation mechanism that provides the high clamping force mode. In many embodiments, the second actuation mechanism is non-back-drivable. In both modes, the position of the jaw members is obtained by the PSM coupled with end effector 188. From the positional data obtained by the PSM during grasping of a body tissue with the end effector, Processor 191 can determine the separation parameter and associated prediction of clamping success with the end effector at the clamping force.

Figure 13A:
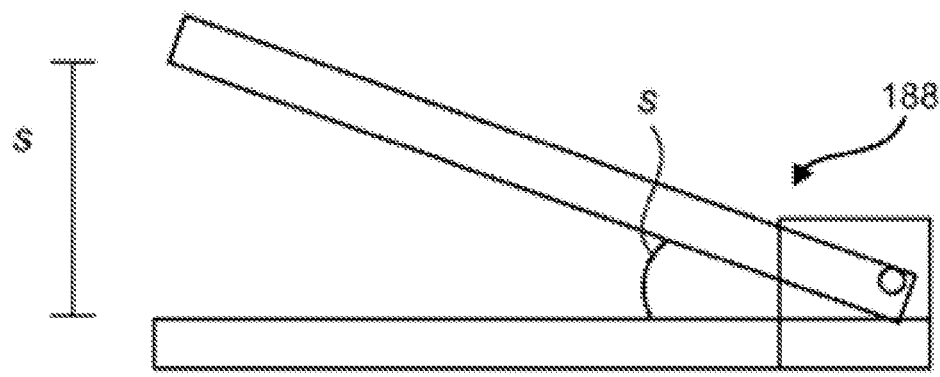
FIGS. 13A through 13C depict an end effector having a first and second jaw and illustrate the grasping separation between jaws in a grasping and clamping configuration, in accordance with many embodiments.
Figure 13B:
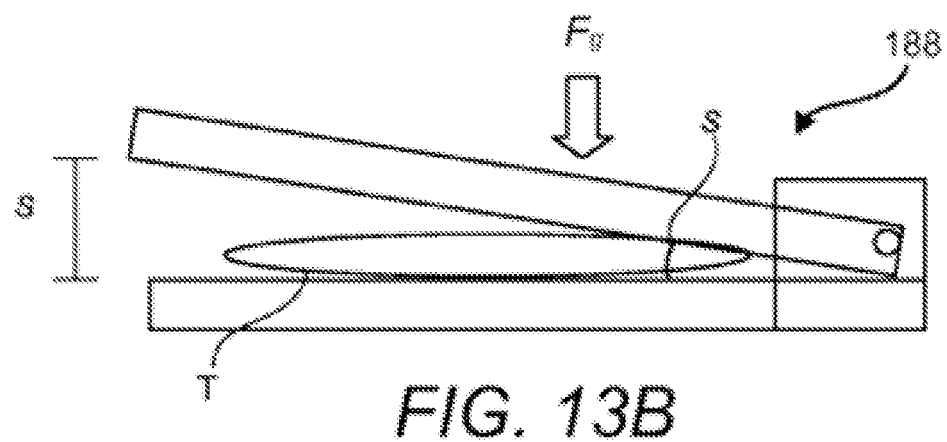
Figure 13C:
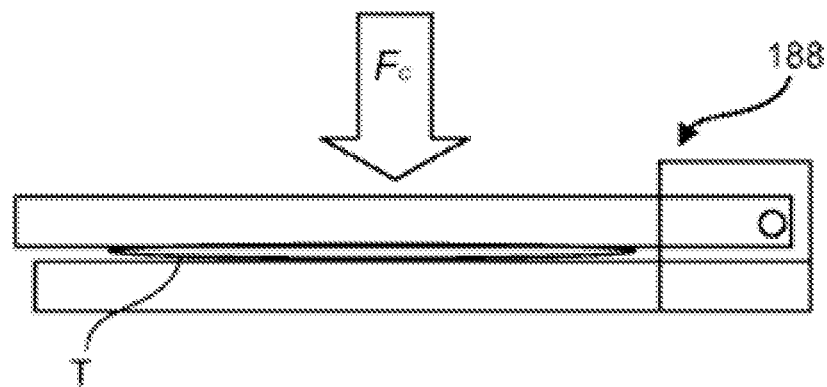

FIGS. 13A-13C illustrate an example of the separation parameter end effector 188 and depicts end effector 188 in both the grasping and clamping positions. FIG. 13A depicts the jaws of end effector 188 wherein the separation parameter (s) is a distance between the tips of the jaw members or may be an angle between jaw members. FIG. 13B illustrates end effector 188 grasping a body tissue (T) between jaw members at grasping force (Fg). In this embodiment, the system measures the separation parameter when the body tissue T is grasped between jaw members at known force Fg. In response, the system provides an indication on the user interface as to whether clamping of the grasped body tissue T at a higher clamping force (Fc) is more likely than not. The indication of the likelihood of clamping success may be based, in whole or in part, on the separation parameter, but may also be based on additional factors, including but not limited to: a type of body tissue (T) (e.g. bowel, stomach), a thickness of the body tissue, a desired clamping force Fc, and a desired separation between jaw members in the fully clamped state. For example, in one embodiment, the claimed system may provide an indication as to the likelihood of clamping the grasped tissue at the clamping force Fc in response to the grasping separation parameter being less than a threshold or desired grasping separation. Alternatively, if the measured separation is greater than the predetermined separation parameter, then the system may provide an indication to the user that clamping may likely not be successful. The predetermined separation parameter may vary according to any of the above stated additional factors. FIG. 13C illustrates end effector 188 having successfully clamped body tissue T between jaw members at clamping force Fc, the clamping force being within a desired range of forces greater than grasping force Fg.

Figure 14A:
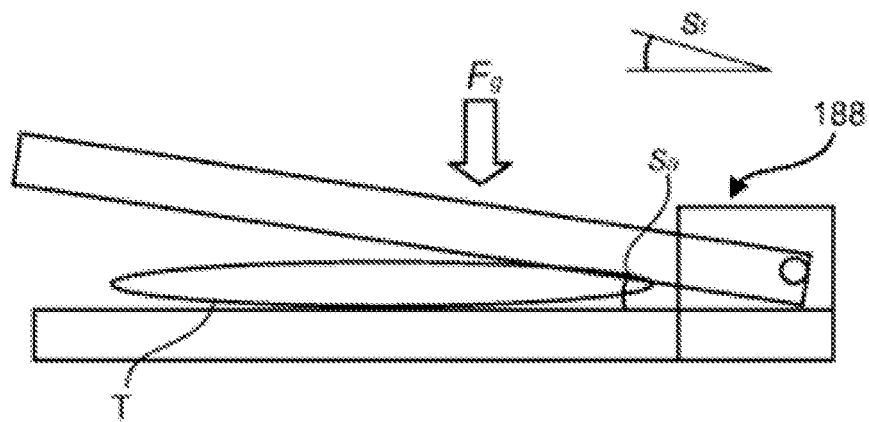
FIGS. 14A-14B illustrate an end effector in a grasping configuration, in accordance with many embodiments.
Figure 14B:
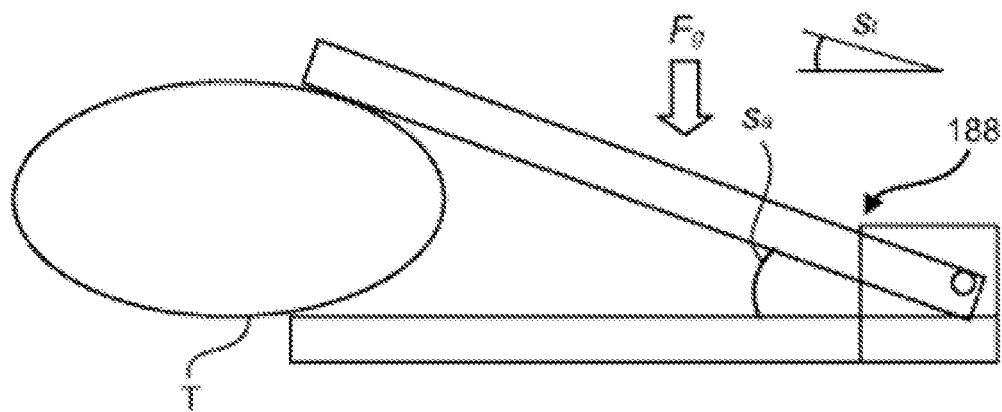

FIGS. 14A-14B illustrate two examples of end effector 188 having grasped body tissue T at grasping force Fg. FIG. 14A depicts an example wherein the actual separation (sa) between the jaws of end effector 188 when grasping the tissue is less than the predetermined grasping separation or target separation (st) as determined for a clamping prediction at a given desired clamping force Fc and/or desired clamping separation. In this example, the system would predict successful clamping and provide an indication of the prediction to the Surgeon on the user interface. FIG. 14B depicts an example wherein the body tissue is positioned such that clamping may not be successful due to tissue slippage or insufficient tissue between the jaws of the end effector. In this example, the actual measured separation (sa) between the jaws of end effector 188 is greater than the predetermined separation or target separation (st) as determined for a clamping prediction at a given clamping force Fc and/or clamping separation. In this embodiment, the system would predict that clamping would likely not be successful and provide an indication of the prediction to the Surgeon on the user interface. After providing an indication that clamping would likely not be successful, the system may prevent the Surgeon from clamping, absent additional input from the user.

Figure 15A:
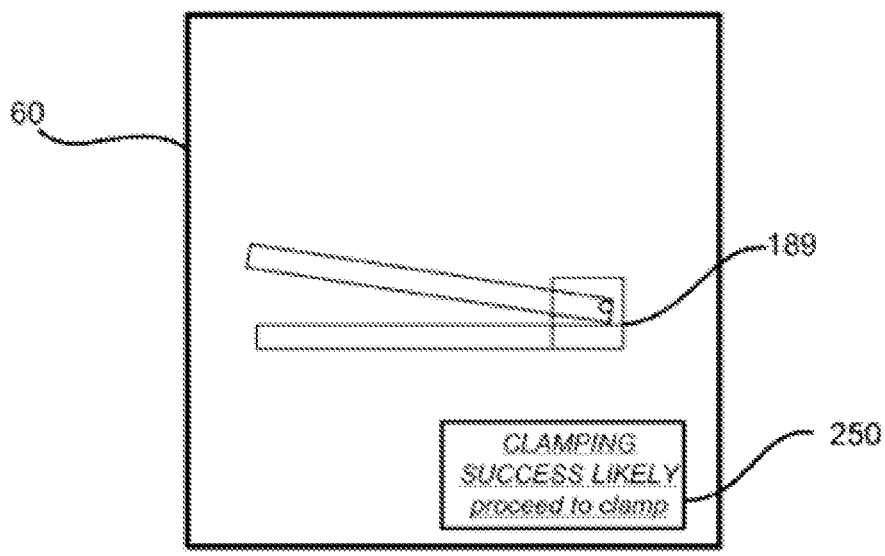
FIGS. 15A-15B illustrate the user interface assembly having an indicator of a prediction of tissue clamping, in accordance with many embodiments.
Figure 15B:
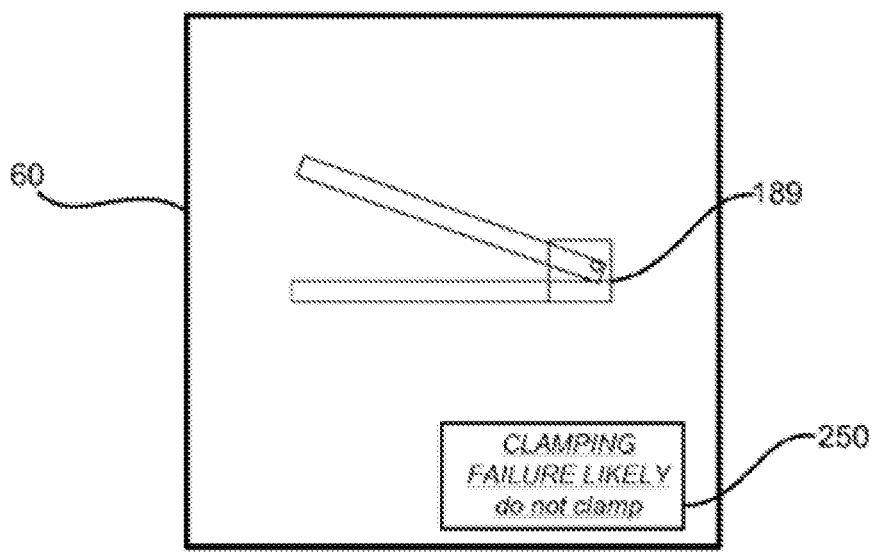

FIGS. 15A-15B illustrate the indication on the user interface Display 60 of System 10 as to whether clamping of grasped tissue would likely be successful. Typically, the user interface Display 60 images and/or visual representations of the surgical tool end effectors during the surgery in addition to the indicators of clamping predictions. The indication of clamping prediction may be superimposed over the images on the user interface display during the surgical procedure so as to seamlessly incorporate the feature into the surgical procedure. Preferably, the clamping prediction indicators only appear when the Surgeon effects grasping of the tissue in preparation for clamping. The indication of clamping prediction facilitates successful clamping of body tissue by the Surgeon during surgery, while minimizing the potential for tissue damage from unsuccessful clamping. FIG. 15A depicts Display 60 with the clamping prediction indicator 250 superimposed on the lower right area of the screen, wherein the indicator predicts clamping is more likely than not. FIG. 15B depicts Display 60 with the clamping prediction indicator 250 superimposed on the lower right area of the screen, wherein the indicator indicates a prediction that clamping will likely not be successful. Often, the Surgeon will not be able to visualize the entire surgical tool with an endoscope due to interference from the body tissue, or the Surgeon may be viewing visual representations of the tools. In FIGS. 15A-15B, the graphical representations of the jaws of end effector 189 on Display 160 are exaggerated and, generally, the Surgeon may not be able to ascertain whether clamping will be successful solely from viewing the images of the surgical tools on Display 60.

Figure 16A:
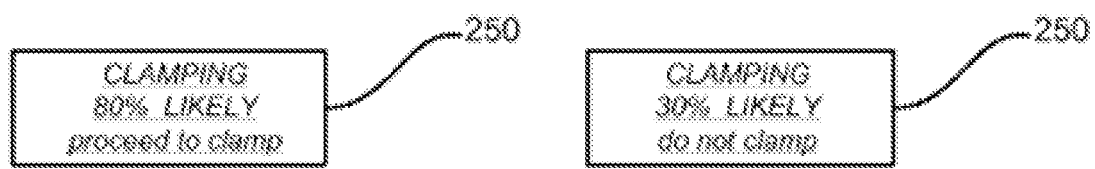
FIGS. 16A-16B illustrate examples of indicators of tissue clamping predictions, in accordance with many embodiments.
Figure 16B:

FIG. 16A-16B illustrate additional examples of the clamping prediction indicator 250. FIG. 16A depicts an example of an indicator wherein the clamping prediction is a gradient of likely clamping success. The system and methods may determine a prediction within the gradient based on various factors, including but not limited to: the difference between the actual separation and the predetermined target separation between jaws grasping the tissue, a type of tissue, a thickness of the tissue, or the desired clamping force and/or clamping separation. For example, the predetermined separation when the jaws are grasped tissue may be a range of acceptable grasping separations, and the further outside the range of predetermined grasping separation the actual measured grasping separation is, the less likely clamping success will be. For example, in one embodiment, if actual measured separation is within 0-2 degrees, then the system will display an indicator of 99% likelihood of clamping success. As the measured separation increases from 2-8 degrees, the likelihood decreases in a monotonically decreasing relationship, such as from 99% down to 10%. FIG. 16B depicts an embodiment having an indicator which toggles between two settings, a predicted clamping success setting and a predicted clamping failure setting. In this example, the indicator is simply a light that when lit indicates that clamping is more likely than not, and when dark indicates that clamping success is not likely.

Figure 17:
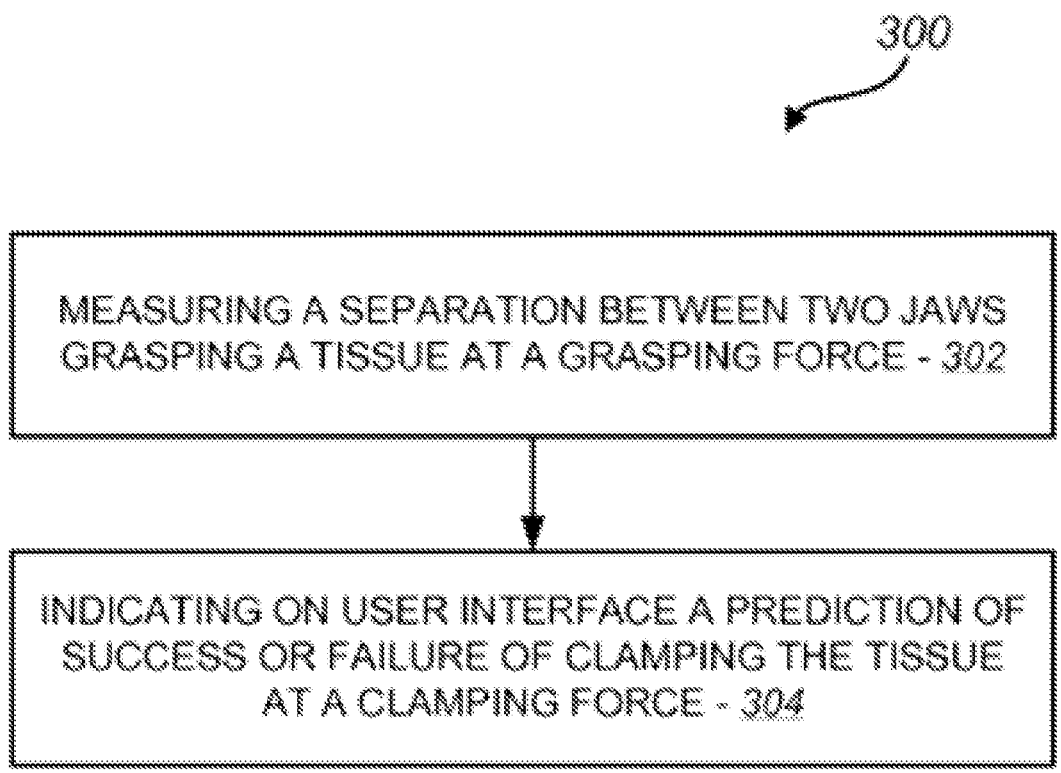
FIGS. 17-19 illustrate methods, in accordance with many embodiments.
Figure 18:
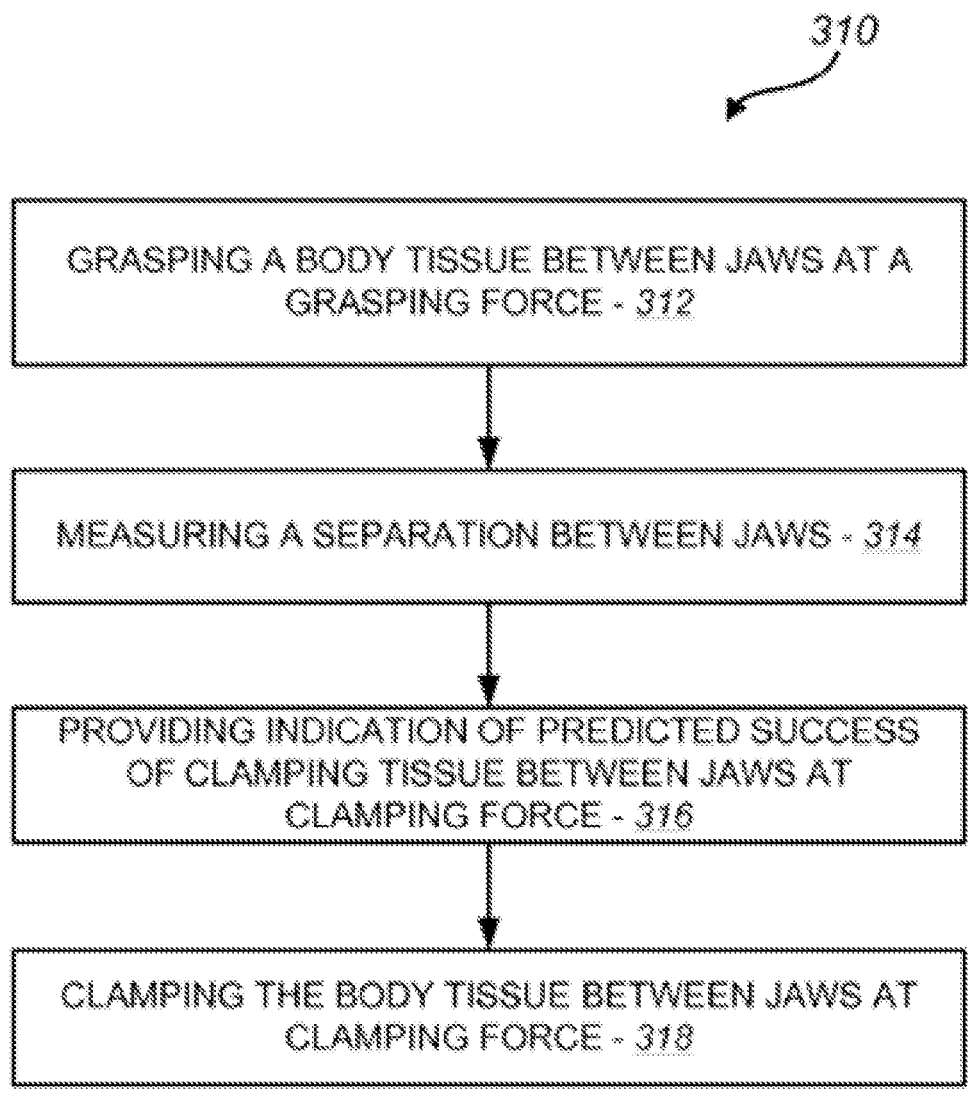
Figure 19:
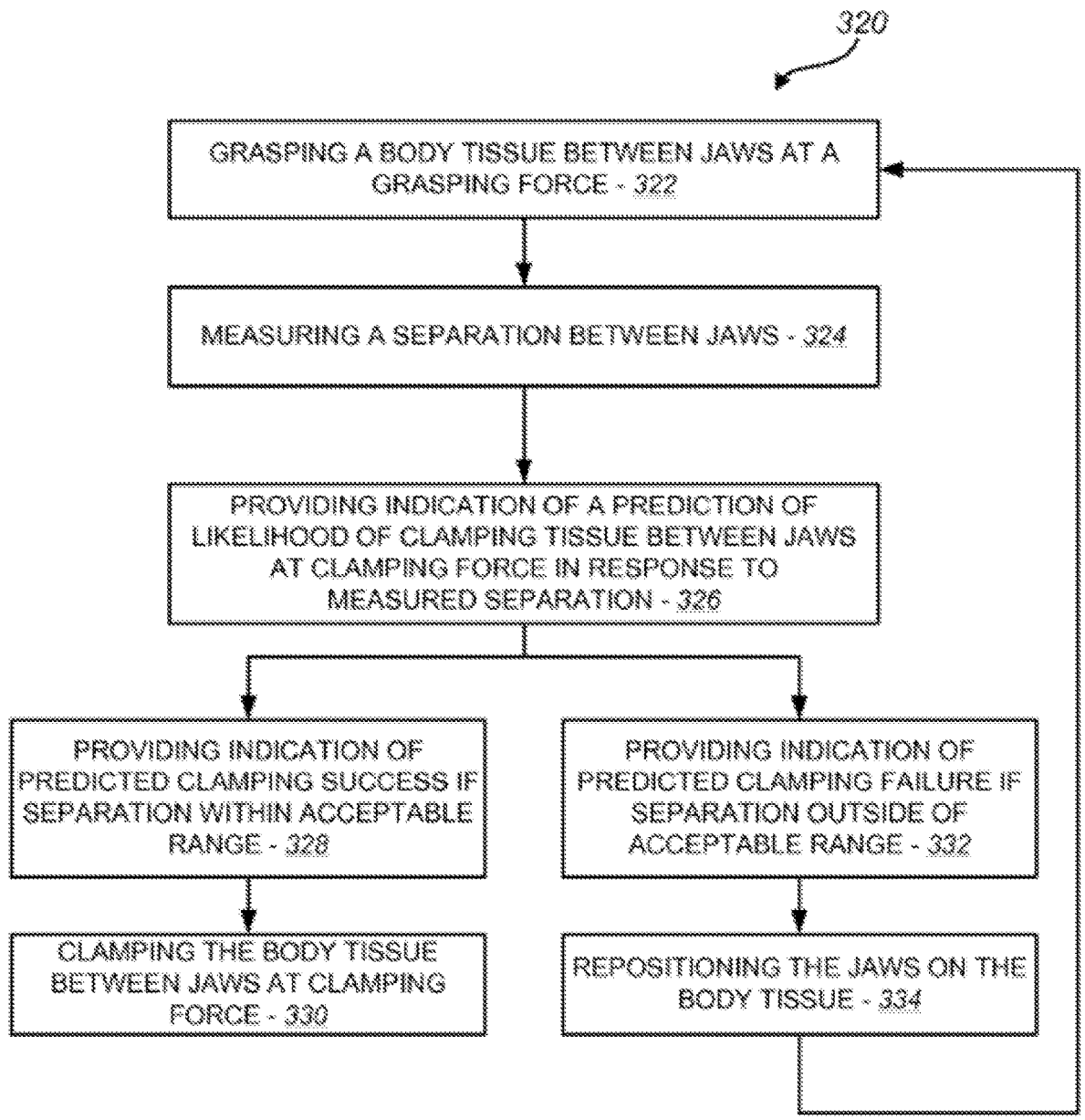

FIGS. 17-19 graphically illustrate embodiments of the claimed methods. FIG. 17 is a simplified representation of exemplary method 300. Method 300 includes a step 302 of measuring a separation between two jaws grasping a tissue at a known grasping force and a step 304 of indicating on a user interface that clamping success or failure is likely when clamping the grasped tissue between the two jaws at a higher clamping force. FIG. 18 is a simplified representation of a method 310 which further includes the step 312 of grasping a body tissue between jaws at a grasping force by the system typically in response to a command from a user and a step 318 of clamping the body tissue between the jaws at the clamping force in response to a command from a user to clamp the tissue after the system has measured the separation between jaws and provided an indication of predicted clamping success in steps 314 and 316, respectively. FIG. 19 is a simplified representation of a method 320 which further includes the step 334 repositioning the jaws on the body tissue in response to a command from a user to reposition the jaws after the system has performed step 332 of providing an indication that clamping success is likely.

Figure 20:
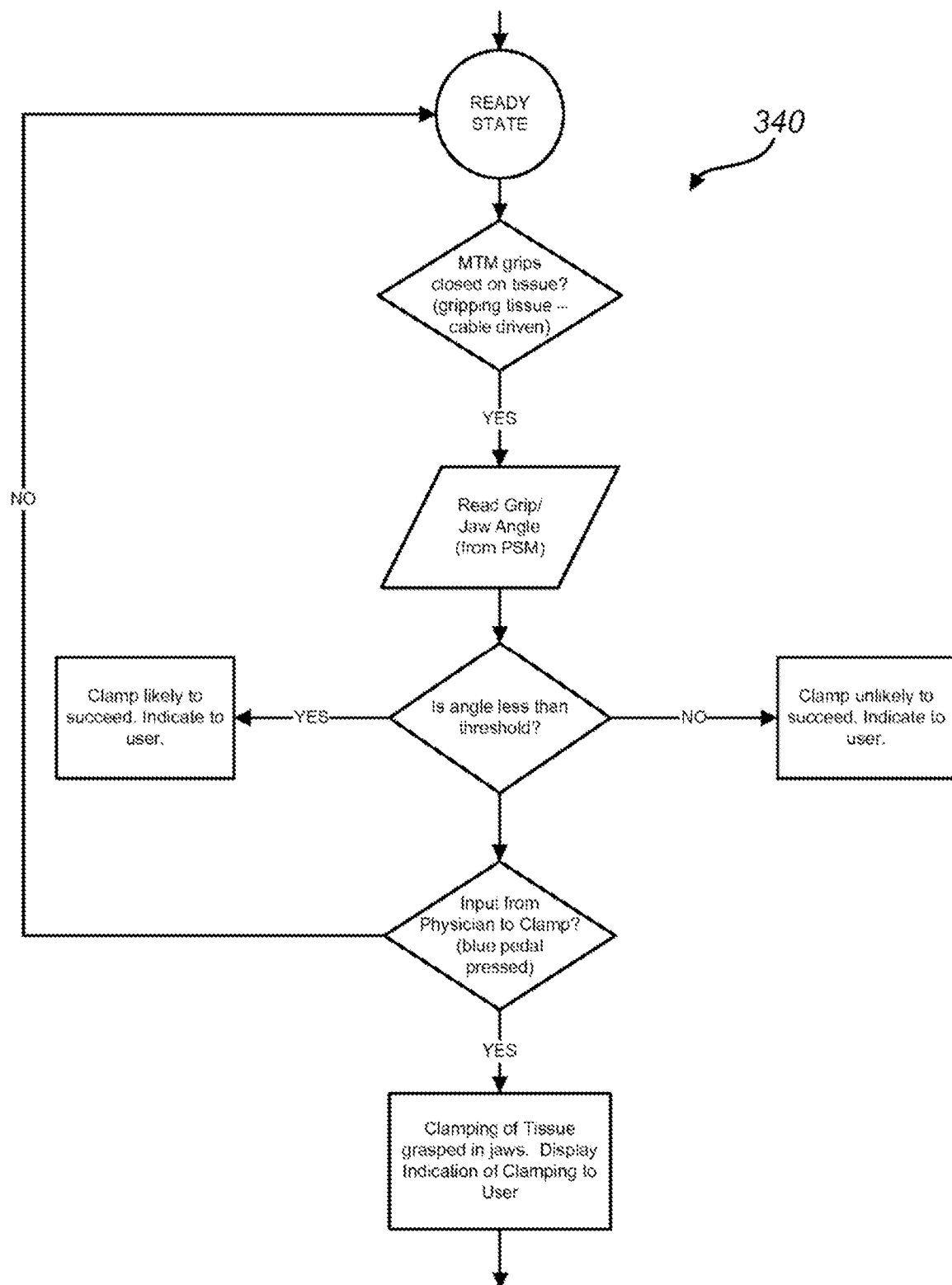
FIGS. 20-21 illustrate flow charts utilizing methods in accordance with many embodiments.
Figure 21:
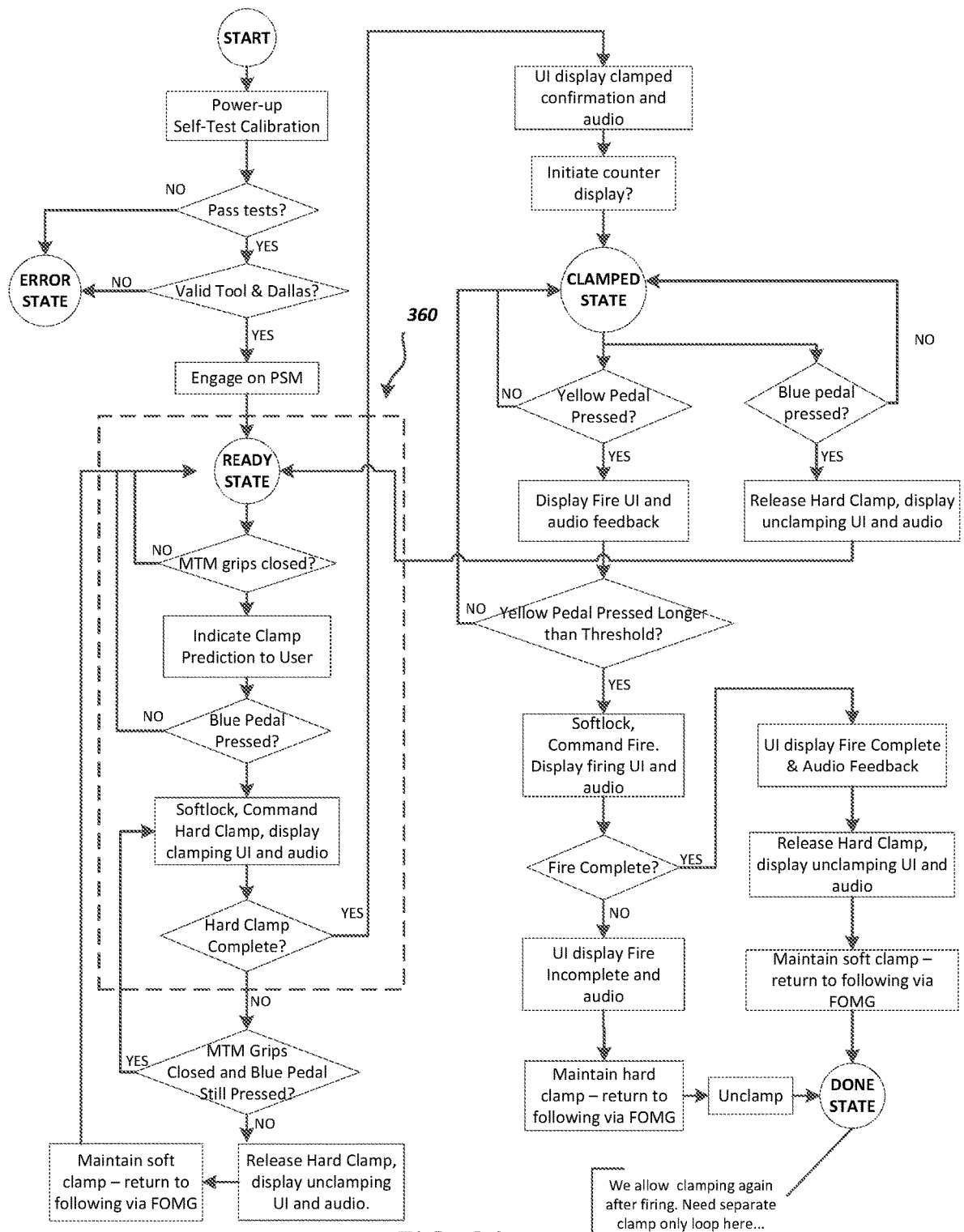

FIGS. 20-21 depict flowcharts illustrating embodiments of the claimed methods. FIG. 20 is a flow chart showing an embodiment of the claimed method wherein the system reads the separation (jaw angle) from the PSM after the body tissue has been grasped between the jaws (MTM grips closed on tissue). If the separation (angle) is less than the predetermined separation (threshold angle), then the system indicates to the user that clamping is likely to succeed. If the separation (angle) is not less than the predetermined separation (threshold), then the system indicates to the user that clamping is unlikely to succeed. If the user provides an input to the system to clamp (blue pedal pressed), then the system proceeds with clamping of the tissue grasped within the jaws. FIG. 20 is a flow chart showing an embodiment of the claimed method incorporated into a surgical system for clamping and sealing a body tissue by firing a staple into the clamped tissue. In FIGS. 20-21, the systems may require user input, such as pressing a blue or yellow pedal, before performing a selected action.

Figure 22A:
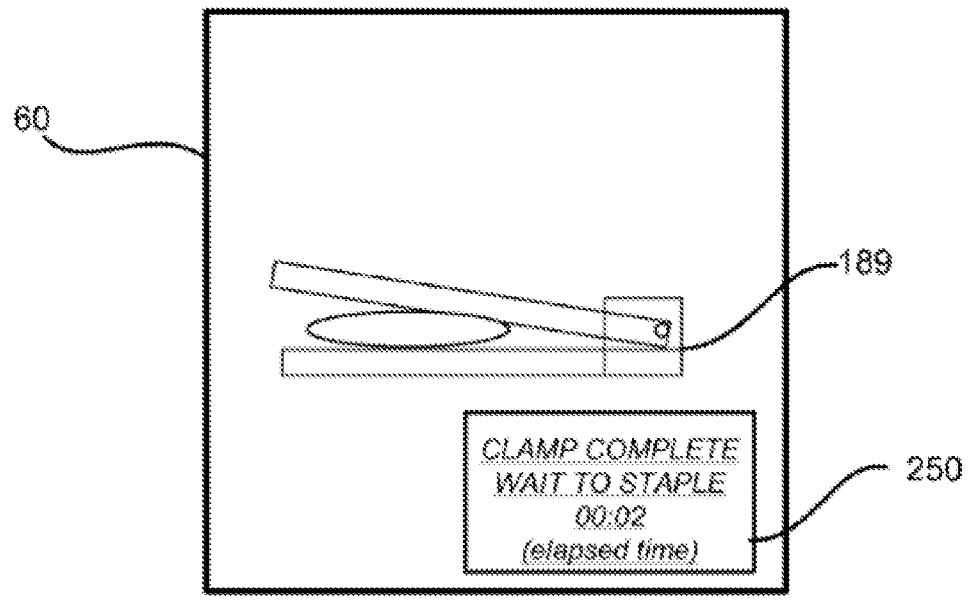
FIGS. 22A-22B illustrate additional examples of indicators in accordance with many embodiments.
Figure 22B:
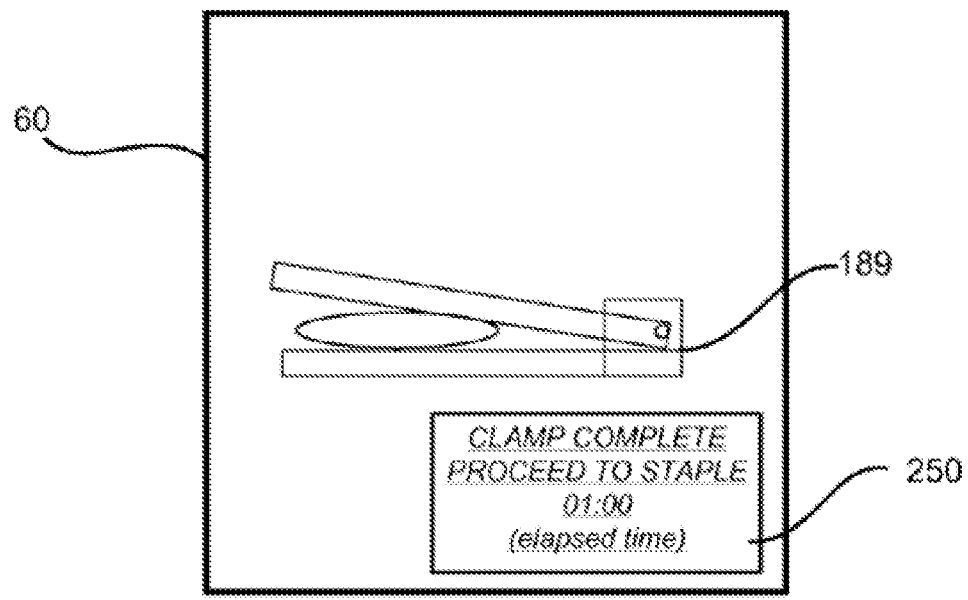

FIGS. 22A-22B illustrate an indication on the user interface Display 60 of System 10 as to whether it is advisable to proceed with stapling of the clamped tissue. The indication may be solely an indicator of whether it is safe to proceed with stapling or may further include a timer for showing an elapsed time (or alternately a countdown) after clamping of the tissue with end effector 189. The indicator 250 may be similar to the indicator illustrated in FIGS. 15A-15B, however, may further include the above described features. The stapling safety indicator and/or timer features are advantageous as allowing the clamped tissue to remain clamped for a specified amount of time before stapling may slightly reduce the thickness of tissue being clamped by squeezing out fluid (e.g., blood) within the tissue to be stapled. Reducing the amount of fluid in the clamped tissue is advantageous as it may reduce the likelihood of bleeding from the staple insertion points during and after stapling. Typically, when tissue is properly clamped between the jaws of the end effector 189, a finite amount of time is required for the clamped tissue to compress (e.g., fluids squish out from the tissue between the jaws) before stapling is initiated. The amount of time needed for sufficient compression and reduction of fluid may vary according to the type and size of staple, the type of stapler and/or clamp, as well as the type and thickness of the tissue being clamped. For example, in performing staple of a bowel tissue, it has been shown that waiting for at least one minute after clamping before stapling of the tissue significantly reduces the amount of bleeding resulting from stapling; however one of skill in the art would appreciate that the duration of time to wait could be less than one minute or greater than one minute, often depending on the procedure and tissue to be stapled. Additionally, maintaining clamping of the tissue after stapling may further reduce bleeding from the stapled tissue and promote hemostasis. The indicator may provide an elapsed time (or a countdown from a recommended wait time) so that the system and/or the Surgeon can recognize that the required time has elapsed and that it is safe to proceed with stapling. In other embodiments, an additional indicator message (e.g., "wait to staple," "proceed with stapling") may aid in indicating to a surgeon that it is advisable to proceed with stapling of the clamped tissue. Such an indication may include, but is not limited to, a change in color in the time indicator display, a change in background color on the display, a light, a sound, or any other indicator suitable for communicating stapling safety and/or clamping duration to the Surgeon. The recommended clamping wait times may be pre-set in the system according to any of the variables of the procedure, or alternatively, may be input by the Surgeon.

In FIG. 22A of the above described embodiment, the Surgeon has successfully clamped the tissue with the jaws of end effector 189, a representation of which is visible on the Display 60. Indicator 250 in the lower right corner of the Display 60 indicates that clamping has been completed and further instructs the surgeon with the message "Wait to Staple," while a timer indicates the time that has elapsed since successful clamping of the tissue. In this embodiment, the recommended time to wait before stapling is one minute. As shown in FIG. 22B, after one minute has elapsed, the indicator 250 displays the elapsed time with the message "Proceed to Staple," after which the surgeon may proceed with stapling of the clamped tissue. In an alternate embodiment, the timer may restart after stapling of the tissue so as to allow a Surgeon to maintain clamping on the stapled tissue.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

What is claimed is:

1. An apparatus comprising:
an end effector for grasping a material;
a drive system coupled to the end effector; and
a processor configured to:
use the drive system to grasp the material using the end effector;
determine a grasping separation parameter of the end effector;
determine, based on the determined grasping separation parameter, a prediction of success or failure in configuring the end effector for firing a staple through the material; and
based on the determined grasping separation parameter, output an indicator of whether conditions are safe to proceed with stapling of the material grasped by the end effector.

2. The apparatus of claim 1, wherein:
the end effector comprises a first jaw and a second jaw for grasping the material; and
the grasping separation parameter is a distance between the first jaw and the second jaw or an angle between the first jaw and the second jaw.

3. The apparatus of claim 1, wherein the determined grasping separation parameter is determined based on one or more of an angle of articulation of the end effector, a thickness of the material, a type of the material, a characteristic of the material, a length of a staple to be applied by the end effector, or a size of the staple.

4. The apparatus of claim 1, wherein the processor is further configured to delay firing of a staple for a predetermined period of time after clamping of the material.

5. The apparatus of claim 4, wherein the predetermined period of time is determined based on one or more of a type of the end effector, a thickness of the material, a type of the material, a size of the staple, or a type of the staple.

6. The apparatus of claim 4, wherein the indicator further comprises an amount of time since the clamping of the material or a countdown of the predetermined period of time.

7. The apparatus of claim 1, wherein the indicator further comprises an audio sound, a haptic response, or a combination of the audio sound and the haptic response.

8. The apparatus of claim 1, wherein the indicator comprises a visual element that toggles between a wait indication and a safe to proceed indication.

9. The apparatus of claim 1, wherein the processor is further configured to indicate a change in status of the indicator using a change in color of the indicator, an audio sound, or a combination of the change in color and the audio sound.

10. The apparatus of claim 1, wherein the indicator further indicates a likelihood of success or failure in clamping the material at a clamping force.

11. A method comprising:
using, by a processor, a drive system to grasp a material using an end effector;
determining, by the processor, a grasping separation parameter of the end effector;
determining, based on the determined grasping separation parameter, a prediction of success or failure in configuring the end effector for firing a staple through the material; and
based on the determined grasping separation parameter, output an indicator of whether conditions are safe to proceed with stapling of the material grasped by the end effector.

12. The method of claim 11, wherein:
the end effector comprises a first jaw and a second jaw for grasping the material; and
the grasping separation parameter is a distance between the first jaw and the second jaw or an angle between the first jaw and the second jaw.

13. The method of claim 11, wherein the determined grasping separation parameter is determined based on one or more of an angle of articulation of the end effector, a thickness of the material, a type of the material, a characteristic of the material, a length of a staple to be applied by the end effector, or a size of the staple.

14. The method of claim 11, further comprising, delaying, by the processor, firing of a staple for a predetermined period of time after clamping of the material.

15. The method of claim 14, wherein the predetermined period of time is determined based on one or more of a type of the end effector, a thickness of the material, a type of the material, a size of the staple, or a type of the staple.

16. The method of claim 14, wherein the indicator further comprises an amount of time since the clamping of the material or a countdown of the predetermined period of time.

17. The method of claim 11, wherein the indicator further comprises an audio sound, a haptic response, or a combination of the audio sound and the haptic response.

18. The method of claim 11, wherein the indicator further comprises a visual element that toggles between a wait indication and a safe to proceed indication.

19. The method of claim 11, further comprising indicating, by the processor, a change in status of the indicator using a change in color of the indicator, an audio sound, or a combination of the change in color and the audio sound.

20. The method of claim 11, wherein the indicator further indicates a likelihood of success or failure in clamping the material at a clamping force.

* * * * *